(12) United States Patent
Cagle et al.

(10) Patent No.: US 10,913,145 B2
(45) Date of Patent: Feb. 9, 2021

(54) CART FOR ROBOTIC ARMS AND METHOD AND APPARATUS FOR CARTRIDGE OR MAGAZINE LOADING OF ARMS

(71) Applicant: Verb Surgical Inc., Mountain View, CA (US)

(72) Inventors: David James Cagle, Belmont, CA (US); Wayne Grout, San Francisco, CA (US); Seung Mo Lim, Santa Cruz, CA (US); Karen Shakespear Koenig, San Jose, CA (US); Robert T. Wiggers, Belmont, CA (US)

(73) Assignee: Verb Surgical Inc., Santa Clara, CA (US)

( * ) Notice: Subject to any disclaimer, the term of this patent is extended or adjusted under 35 U.S.C. 154(b) by 370 days.

(21) Appl. No.: 15/785,291

(22) Filed: Oct. 16, 2017

(65) Prior Publication Data

US 2018/0361568 A1  Dec. 20, 2018

Related U.S. Application Data

(60) Provisional application No. 62/522,494, filed on Jun. 20, 2017.

(51) Int. Cl.
*F16M 1/00* (2006.01)
*B25J 9/00* (2006.01)
(Continued)

(52) U.S. Cl.
CPC ............. *B25J 9/0084* (2013.01); *A61B 34/30* (2016.02); *A61B 50/13* (2016.02); *A61B 50/20* (2016.02);
(Continued)

(58) Field of Classification Search
CPC ........ A61B 50/13; A61B 34/30; B25J 9/0084; B25J 9/0009; B60P 1/6418; B62B 3/00; B62B 3/005; B62B 3/04
(Continued)

(56) References Cited

U.S. PATENT DOCUMENTS 5,351,676 A * 10/1994 Putman ................... B25J 9/042
200/5 R
5,876,325 A    3/1999 Mizuno et al.
(Continued)

FOREIGN PATENT DOCUMENTS

CA    2913943 A1    12/2014
EP    2145586 A1    1/2010
(Continued)

OTHER PUBLICATIONS

International Preliminary Report on Patentability for International Application No. PCT/US2018/033056, dated Dec. 5, 2019, 6 pages.
(Continued)

*Primary Examiner* — Todd M Epps
(74) *Attorney, Agent, or Firm* — Womble Bond Dickinson (US) LLP

(57) ABSTRACT

Apparatus and methods for providing a robotic arm cart for transporting, delivering, and securing robotic arms to a surgical table having a tabletop on which a patient can be disposed are described herein. In some embodiments described herein an arm cart can contain multiple robotic arms. A robotic arm can be selected and moved from a storage position within the arm cart to a deployment position in which at least a portion of that robotic arm protrudes from the arm cart. A robotic arm in a deployment position can be coupled to a surgical table and decoupled from the arm cart.

10 Claims, 14 Drawing Sheets

(51) Int. Cl.
*B60P 1/64* (2006.01)
*B62B 3/00* (2006.01)
*A61B 50/13* (2016.01)
*A61B 50/20* (2016.01)
*A61B 90/50* (2016.01)
*A61B 50/30* (2016.01)
*A61B 34/30* (2016.01)
*B25J 19/00* (2006.01)
*B62B 3/04* (2006.01)
*A61B 90/57* (2016.01)

(52) U.S. Cl.
CPC .............. *A61B 50/30* (2016.02); *A61B 90/50* (2016.02); *B25J 9/0009* (2013.01); *B25J 19/007* (2013.01); *B60P 1/6418* (2013.01); *B62B 3/00* (2013.01); *B62B 3/005* (2013.01); *B62B 3/04* (2013.01); *A61B 2090/571* (2016.02); *B62B 2203/04* (2013.01); *B62B 2203/07* (2013.01)

(58) Field of Classification Search
USPC ............. 248/645, 129; 606/139; 318/568.11, 318/568.12
See application file for complete search history.

(56) References Cited

U.S. PATENT DOCUMENTS

| | | | |
|---|---|---|---|
| 6,132,368 A | 10/2000 | Cooper | |
| 6,246,200 B1 * | 6/2001 | Blumenkranz | ........ B25J 9/1689 128/DIG. 7 |
| 6,331,181 B1 | 12/2001 | Tierney et al. | |
| 6,346,072 B1 | 2/2002 | Cooper | |
| 6,450,978 B1 | 9/2002 | Brosseau et al. | |
| 6,451,027 B1 | 9/2002 | Cooper et al. | |
| 6,535,756 B1 | 3/2003 | Simon et al. | |
| 6,587,750 B2 | 7/2003 | Akui et al. | |
| 6,608,628 B1 | 8/2003 | Ross et al. | |
| 6,659,939 B2 | 12/2003 | Moll et al. | |
| 6,768,496 B2 | 7/2004 | Bieger et al. | |
| 6,788,018 B1 | 9/2004 | Blumenkranz | |
| 6,866,671 B2 | 3/2005 | Tierney et al. | |
| 6,920,347 B2 | 7/2005 | Simon et al. | |
| 6,962,581 B2 | 11/2005 | Thoe | |
| 6,995,744 B1 | 2/2006 | Moore et al. | |
| 7,008,362 B2 | 3/2006 | Fitzgibbon | |
| 7,012,203 B2 | 3/2006 | Hanson et al. | |
| 7,048,745 B2 | 5/2006 | Tierney et al. | |
| 7,206,627 B2 | 4/2007 | Abovitz et al. | |
| 7,217,269 B2 | 5/2007 | El-Galley et al. | |
| 7,277,120 B2 | 10/2007 | Gere et al. | |
| 7,317,955 B2 | 1/2008 | McGreevy | |
| 7,331,967 B2 | 2/2008 | Lee et al. | |
| 7,357,774 B2 | 4/2008 | Cooper | |
| 7,369,116 B2 | 5/2008 | Logue | |
| 7,379,790 B2 | 5/2008 | Toth et al. | |
| 7,498,532 B2 | 3/2009 | Kuhner et al. | |
| 7,524,320 B2 | 4/2009 | Tierney et al. | |
| 7,554,526 B2 | 6/2009 | Logue | |
| 7,594,912 B2 | 9/2009 | Cooper et al. | |
| 7,666,191 B2 | 2/2010 | Orban, III et al. | |
| 7,699,855 B2 | 4/2010 | Anderson et al. | |
| 7,727,244 B2 | 6/2010 | Orban, III et al. | |
| 7,768,702 B2 | 8/2010 | Hirose et al. | |
| 7,781,941 B2 | 8/2010 | Horvath et al. | |
| 7,783,133 B2 | 8/2010 | Dunki-Jacobs et al. | |
| 7,789,874 B2 | 9/2010 | Yu et al. | |
| 7,789,875 B2 | 9/2010 | Brock et al. | |
| 7,819,885 B2 | 10/2010 | Cooper | |
| 7,840,042 B2 | 11/2010 | Kriveshko et al. | |
| 7,843,158 B2 | 11/2010 | Prisco | |
| 7,853,305 B2 | 12/2010 | Simon et al. | |
| 7,865,266 B2 | 1/2011 | Moll et al. | |
| 7,883,458 B2 | 2/2011 | Hamel | |
| 7,907,166 B2 | 3/2011 | Lamprecht et al. | |
| 7,922,439 B2 | 4/2011 | Kato | |
| 7,947,050 B2 | 5/2011 | Lee et al. | |
| 7,955,322 B2 | 6/2011 | Devengenzo et al. | |
| 7,983,793 B2 | 7/2011 | Toth et al. | |
| 8,004,229 B2 | 8/2011 | Nowlin et al. | |
| 8,062,288 B2 | 11/2011 | Cooper et al. | |
| 8,079,950 B2 | 12/2011 | Stern et al. | |
| 8,086,008 B2 | 12/2011 | Coste-Maniere et al. | |
| 8,095,200 B2 | 1/2012 | Quaid et al. | |
| 8,100,133 B2 | 1/2012 | Mintz et al. | |
| 8,105,338 B2 | 1/2012 | Anderson et al. | |
| 8,120,301 B2 | 2/2012 | Goldberg et al. | |
| 8,126,114 B2 | 2/2012 | Naylor et al. | |
| 8,131,031 B2 | 3/2012 | Lloyd | |
| 8,142,447 B2 | 3/2012 | Cooper et al. | |
| 8,147,503 B2 | 4/2012 | Zhao et al. | |
| 8,155,479 B2 | 4/2012 | Hoffman et al. | |
| 8,190,238 B2 | 5/2012 | Moll et al. | |
| 8,202,278 B2 | 6/2012 | Orban, III et al. | |
| 8,206,406 B2 | 6/2012 | Orban et al. | |
| 8,256,319 B2 | 9/2012 | Cooper et al. | |
| 8,332,072 B1 | 12/2012 | Schaible et al. | |
| 8,391,954 B2 | 3/2013 | Quaid, III | |
| 8,395,342 B2 | 3/2013 | Prisco | |
| 8,398,541 B2 | 3/2013 | DiMaio et al. | |
| 8,418,073 B2 | 4/2013 | Mohr et al. | |
| 8,469,947 B2 | 6/2013 | Devengenzo et al. | |
| 8,473,031 B2 | 6/2013 | Nixon et al. | |
| 8,504,136 B1 | 8/2013 | Sun et al. | |
| 8,506,555 B2 | 8/2013 | Morales | |
| 8,508,173 B2 | 8/2013 | Goldberg et al. | |
| 8,521,331 B2 | 8/2013 | Itkowitz | |
| 8,527,094 B2 | 9/2013 | Kumar et al. | |
| 8,541,970 B2 | 9/2013 | Nowlin et al. | |
| 8,562,594 B2 | 10/2013 | Cooper et al. | |
| 8,594,841 B2 | 11/2013 | Zhao et al. | |
| 8,600,551 B2 | 12/2013 | Itkowitz et al. | |
| 8,620,473 B2 | 12/2013 | Diolaiti et al. | |
| 8,624,537 B2 | 1/2014 | Nowlin et al. | |
| 8,628,518 B2 | 1/2014 | Blumenkranz et al. | |
| 8,634,957 B2 | 1/2014 | Toth et al. | |
| 8,638,056 B2 | 1/2014 | Goldberg et al. | |
| 8,672,922 B2 | 3/2014 | Loh et al. | |
| 8,682,489 B2 | 3/2014 | Itkowitz et al. | |
| 8,706,184 B2 | 4/2014 | Mohr et al. | |
| 8,715,167 B2 | 5/2014 | Stern et al. | |
| 8,747,288 B2 | 6/2014 | Strotzer et al. | |
| 8,749,189 B2 | 6/2014 | Nowlin et al. | |
| 8,749,190 B2 | 6/2014 | Nowlin et al. | |
| 8,761,337 B2 | 6/2014 | Naylor et al. | |
| 8,786,241 B2 | 7/2014 | Nowlin et al. | |
| 8,806,359 B2 | 8/2014 | Garibaldi et al. | |
| 8,816,628 B2 | 8/2014 | Nowlin et al. | |
| 8,823,308 B2 | 9/2014 | Nowlin et al. | |
| 8,828,023 B2 | 9/2014 | Neff et al. | |
| 8,831,782 B2 | 9/2014 | Itkowitz | |
| 8,870,861 B2 | 10/2014 | El-Galley et al. | |
| 8,888,764 B2 | 11/2014 | Devengenzo et al. | |
| 8,930,027 B2 | 1/2015 | Schaible et al. | |
| 8,939,500 B2 | 1/2015 | Voigt et al. | |
| 8,968,333 B2 | 3/2015 | Yu et al. | |
| 8,989,903 B2 | 3/2015 | Weir et al. | |
| 8,996,173 B2 | 3/2015 | Itkowitz et al. | |
| 9,002,517 B2 | 4/2015 | Bosscher et al. | |
| 9,026,247 B2 | 5/2015 | White et al. | |
| 9,078,686 B2 | 7/2015 | Schena | |
| 9,108,318 B2 | 8/2015 | Diolaiti | |
| 9,129,422 B2 | 9/2015 | Mountney et al. | |
| 9,179,980 B2 | 11/2015 | Yoon | |
| 9,198,731 B2 | 12/2015 | Balaji et al. | |
| 9,215,293 B2 | 12/2015 | Miller | |
| 9,221,172 B2 | 12/2015 | Williamson et al. | |
| 9,232,984 B2 | 1/2016 | Guthart et al. | |
| 9,241,768 B2 | 1/2016 | Sandhu et al. | |
| 9,254,572 B2 | 2/2016 | Strotzer | |
| 9,256,936 B2 | 2/2016 | Jacobs et al. | |
| 9,259,276 B2 | 2/2016 | Mintz et al. | |
| 9,259,282 B2 | 2/2016 | Azizian et al. | |

(56) References Cited

U.S. PATENT DOCUMENTS

| | | | |
|---|---|---|---|
| 9,295,524 | B2 | 3/2016 | Schena et al. |
| 9,320,568 | B2 | 4/2016 | Orban, III et al. |
| 9,333,042 | B2 | 5/2016 | Diolaiti et al. |
| 9,345,546 | B2 | 5/2016 | Toth et al. |
| 9,433,288 | B2 | 9/2016 | Voigt et al. |
| 9,486,159 | B2 | 11/2016 | Coste-Maniere et al. |
| 9,694,839 | B2 * | 7/2017 | Canady .................. A61B 50/13 |
| 10,034,721 | B1 * | 7/2018 | Timm ....................... B62B 3/04 |
| 2002/0133174 | A1 | 9/2002 | Charles et al. |
| 2006/0161136 | A1 | 7/2006 | Anderson et al. |
| 2009/0068620 | A1 | 3/2009 | Knobel et al. |
| 2009/0240370 | A1 | 9/2009 | Nichols et al. |
| 2009/0248041 | A1 | 10/2009 | Williams et al. |
| 2010/0012798 | A1 | 1/2010 | Blum et al. |
| 2012/0154564 | A1 | 6/2012 | Hoffman et al. |
| 2013/0085389 | A1 | 4/2013 | Tsang et al. |
| 2014/0052154 | A1 | 2/2014 | Griffiths et al. |
| 2014/0100588 | A1 | 4/2014 | Blumenkranz et al. |
| 2014/0107627 | A1 | 4/2014 | Blumenkranz et al. |
| 2014/0130810 | A1 | 5/2014 | Azizian et al. |
| 2014/0168073 | A1 | 6/2014 | Chizeck et al. |
| 2014/0171965 | A1 | 6/2014 | Loh et al. |
| 2014/0188131 | A1 | 7/2014 | Toth et al. |
| 2014/0276949 | A1 | 9/2014 | Staunton et al. |
| 2014/0282196 | A1 | 9/2014 | Zhao et al. |
| 2014/0297130 | A1 | 10/2014 | Griffiths et al. |
| 2015/0032126 | A1 | 1/2015 | Nowlin et al. |
| 2015/0045812 | A1 | 2/2015 | Seo |
| 2015/0051733 | A1 | 2/2015 | Nowlin et al. |
| 2015/0190201 | A1 | 7/2015 | Olson |
| 2015/0265356 | A1 | 9/2015 | Schena |
| 2015/0321355 | A1 | 11/2015 | Kishi |
| 2015/0374446 | A1 | 12/2015 | Malackowski et al. |
| 2016/0076992 | A1 | 3/2016 | Gillespie et al. |
| 2016/0140875 | A1 | 5/2016 | Kumar et al. |
| 2016/0157943 | A1 | 6/2016 | Mintz et al. |
| 2016/0166345 | A1 | 6/2016 | Kumar et al. |
| 2016/0184037 | A1 | 6/2016 | Cooper et al. |
| 2016/0242860 | A1 | 8/2016 | Diolaiti et al. |
| 2017/0000575 | A1 | 1/2017 | Griffiths et al. |
| 2017/0065355 | A1 * | 3/2017 | Ross ..................... A61B 34/30 |
| 2017/0071693 | A1 | 3/2017 | Taylor et al. |
| 2017/0079730 | A1 * | 3/2017 | Azizian .................. A61G 13/02 |
| 2017/0083453 | A1 | 3/2017 | Guildford et al. |
| 2017/0119421 | A1 | 5/2017 | Staunton et al. |
| 2017/0135771 | A1 | 5/2017 | Auld et al. |
| 2017/0312047 | A1 | 11/2017 | Swarup et al. |
| 2018/0042682 | A1 | 2/2018 | Iceman et al. |
| 2018/0078439 | A1 * | 3/2018 | Cagle ..................... A61B 90/57 |
| 2018/0147106 | A1 * | 5/2018 | Soundararajan ....... A61B 34/30 |
| 2018/0271604 | A1 * | 9/2018 | Grout .................... F16B 21/165 |
| 2018/0333215 | A1 * | 11/2018 | Timm .................... A61B 90/50 |
| 2018/0361568 | A1 * | 12/2018 | Cagle .................... B60P 1/6418 |

FOREIGN PATENT DOCUMENTS

| | | |
|---|---|---|
| JP | 02-059468 A | 2/1990 |
| JP | 04-019729 A | 1/1992 |
| JP | 06-297378 A | 10/1994 |
| JP | 08-224243 A | 9/1996 |
| JP | 2007-276063 A | 10/2007 |
| JP | 2014-158942 A | 9/2014 |
| JP | 2017-513550 A | 6/2017 |
| RU | 122281 U1 | 11/2012 |
| WO | WO-2014/151621 A1 | 9/2014 |
| WO | WO-2014/152694 A1 | 9/2014 |
| WO | WO-2014/201538 A1 | 12/2014 |
| WO | 2015/142798 A1 | 9/2015 |
| WO | WO2015/142801 A1 | 9/2015 |
| WO | 2015/175203 A1 | 11/2015 |
| WO | WO-2016/048738 A1 | 3/2016 |
| WO | 2016054256 A1 | 4/2016 |
| WO | WO-2016/058079 A1 | 4/2016 |
| WO | WO2016/069661 A1 | 5/2016 |
| WO | WO2017/030848 A1 | 2/2017 |
| WO | WO2017/062391 A1 | 4/2017 |
| WO | 20171085094 A1 | 5/2017 |
| WO | WO2017/083453 A1 | 5/2017 |
| WO | 2018053282 A1 | 3/2018 |

OTHER PUBLICATIONS

International Preliminary Report on Patentability for International Application No. PCT/US2018/034229, dated Dec. 12, 2019, 6 pages.
International Preliminary Report on Patentability for International Application No. PCT/US2018/034945, dated Dec. 12, 2019, 6 pages.
International Preliminary Report on Patentability for International Application No. PCT/US2018/036566, dated Jan. 2, 2020, 6 pages.
U.S. Appl. No. 15/717,599, filed Sep. 27, 2017, by Timm et al.
U.S. Appl. No. 15/785,341, filed Oct. 16, 2017, by Timm et al.
U.S. Appl. No. 15/785,331, filed Oct. 16, 2017, by Cagle et al.
U.S. Appl. No. 15/725,093, filed Oct. 4, 2017, by Wiggers.
U.S. Appl. No. 15/822,986, filed Nov. 27, 2017, by Timm et al.
U.S. Appl. No. 15/823,006, filed Nov. 27, 2017, by Timm et al.
U.S. Appl. No. 15/823,042, filed Nov. 27, 2017, by Soundararajan et al.
U.S. Appl. No. 15/706,112, filed Sep. 15, 2017, by Koenig.
U.S. Appl. No. 15/706,087, filed Sep. 15, 2017, by Cagle et al.
U.S. Appl. No. 15/788,730, filed Oct. 19, 2017, by Schaller et al.
International Search Report and Written Opinion of the Searching Authority, dated Aug. 23, 2018, for PCT application No. PCT/US2018034229.
International Search Report and Written Opinion of the Searching Authority, dated Sep. 20, 2018, for PCT application No. PCT/US2018035900.
International Search Report and Written Opinion of the Searching Authority, dated Sep. 13, 2018, for PCT application No. PCT/US2018034945.
International Search Report and Written Opinion of the Searching Authority, dated Sep. 27, 2018, for PCT application No. PCT/US2018036566.
Notice of Allowance and Fees Due (PTOL-85) dated Apr. 4, 2018 for U.S. Appl. No. 15/717,599.
Examination Report No. 1 of the Australian Patent Office dated May 11, 2020, for related Australian Patent Application No. 2018289123.
Australian Examination Report for Australian Application No. 2018276946 dated Jan. 24, 2020, 4 pages.
International Preliminary Report on Patentability for International Application No. PCT/US2018/035900, dated Apr. 9, 2020, 6 pages.
Australian Examination Report for Australian Application No. 2018271773 dated Jan. 31, 2020, 4 pages.
First Examination Report dated Jul. 13, 2020 issued by IP Australia for related Australian Patent Application No. 2018278218.
Notice of Reasons for Refusal of the Japanese Patent Office dated Oct. 27, 2020 for related Japanese Patent Application No. 2019-563190.
Supplementary European Search Report and Search Opinion of the European Patent Office dated Dec. 14, 2020 for related European Patent Application No. 18820247.7.
Notice of Reasons for Refusal of the Japanese Patent Office dated Oct. 27, 2020 for related Japanese Patent Application No. 2019-563141.
Notice of Reasons for Rejection of the Japanese Patent Office dated Nov. 4, 2020 for related Japanese Patent Application No. 2019-563192.
Supplementary European Search Report and Search Opinion of the European Patent Office dated Dec. 11, 2020 for related European Patent Application No. 18810600.9.
Notice of Reasons for Refusal of the Japanese Patent Office dated Dec. 1, 2020 for related Japanese Patent Application No. 2019-563290.
Supplementary European Search Report and Search Opinion of the European Patent Office dated Nov. 19, 2020 for related European Patent Application No. 18806664.1.

(56) References Cited

OTHER PUBLICATIONS

Supplementary European Search Report of the European Patent Office dated Nov. 23, 2020 for related European Patent Application No. 18808974.2.

* cited by examiner

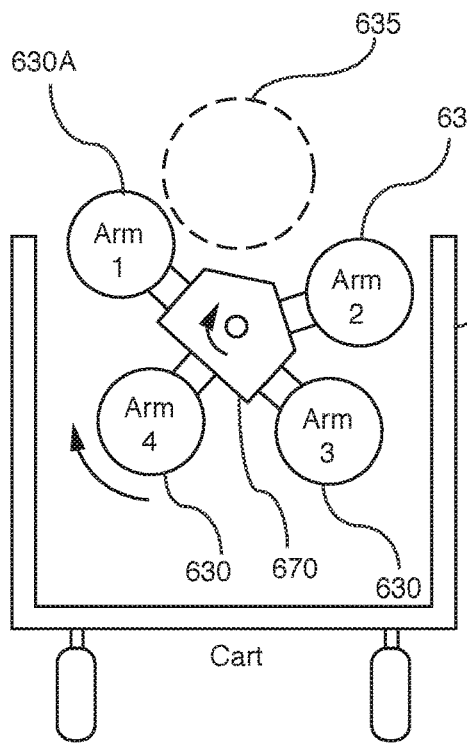 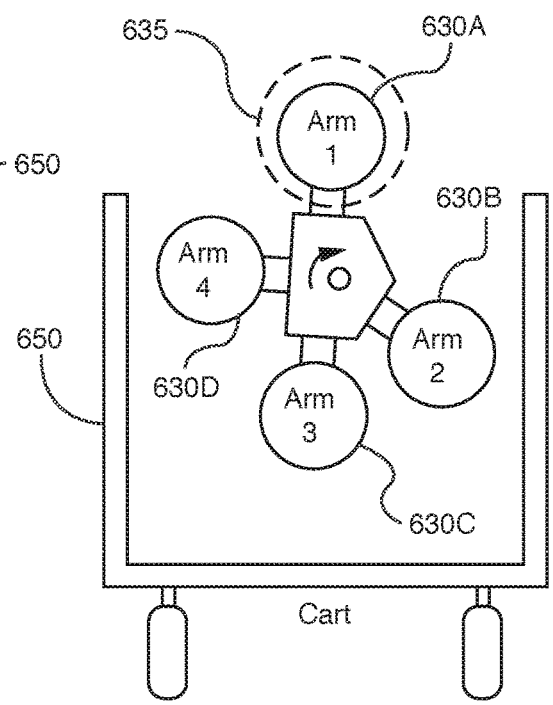
FIG. 6A  FIG. 6B
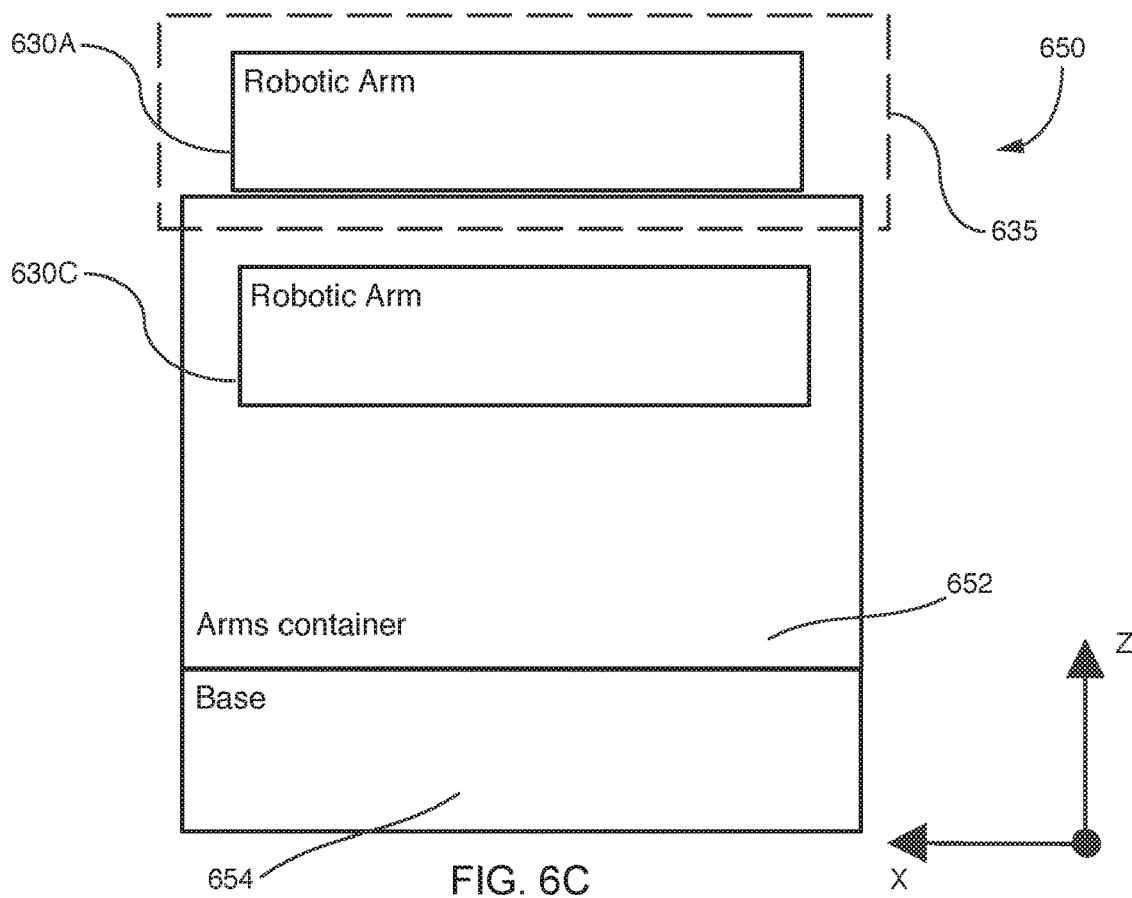
FIG. 6C

CART FOR ROBOTIC ARMS AND METHOD AND APPARATUS FOR CARTRIDGE OR MAGAZINE LOADING OF ARMS

CROSS-REFERENCE TO RELATED APPLICATIONS

This application claims priority to U.S. Patent Application Ser. No. 62/522,494, filed on Jun. 20, 2017, which is hereby incorporated by reference in its entirety.

BACKGROUND

Embodiments described herein relate to apparatus and methods for a robotic arm cart for transporting, delivering, and securing robotic arms to, for example, a surgical table.

SUMMARY

Apparatus and methods for providing a robotic arm cart for transporting, delivering, and securing robotic arms to a surgical table having a tabletop on which a patient can be disposed are described herein. In some embodiments described herein an arm cart can contain multiple robotic arms. A robotic arm can be selected and moved from a storage position within the arm cart to a deployment position in which at least a portion of that robotic arm protrudes from the arm cart. A robotic arm in a deployment position can be coupled to a surgical table and decoupled from the arm cart.

BRIEF DESCRIPTION OF THE DRAWINGS

FIGS. 6A and 6B are front schematic illustrations of an arm cart having a rotary mechanism in two configurations according to an embodiment.

FIG. 6C is a side schematic illustration of the arm cart of FIGS. 6A and 6B with the rotary mechanism in the configuration shown in FIG. 6B.

DETAILED DESCRIPTION

Apparatus and methods for providing a robotic arm cart for transporting, delivering, and securing robotic arms to a surgical table having a tabletop on which a patient can be disposed are described herein. In some embodiments, an apparatus includes an arm cart that can receive and contain multiple robotic arms. Robotic arms within the arm cart can be operable to move between storage positions and deployment positions. For example, robotic arms in storage positions can be entirely disposed within the arm cart, while a robotic arm in a deployment position can at least partially protrude from the arm cart. In some embodiments, robotic arms can be vertically disposed in the storage position and pivoted into a horizontal position such that the robotic arm can be coupled to a surgical table. In other embodiments, a rotary mechanism can simultaneously rotate multiple robotic arms to place a selected robotic arm in a deployment position. Once in the deployment position, the robotic arm can be slid towards the surgical table where that robotic arm can mate with a port or other suitable connecting point. The robotic arm can then be decoupled from the arm cart, and the arm cart can be withdrawn.

Figure 1A:
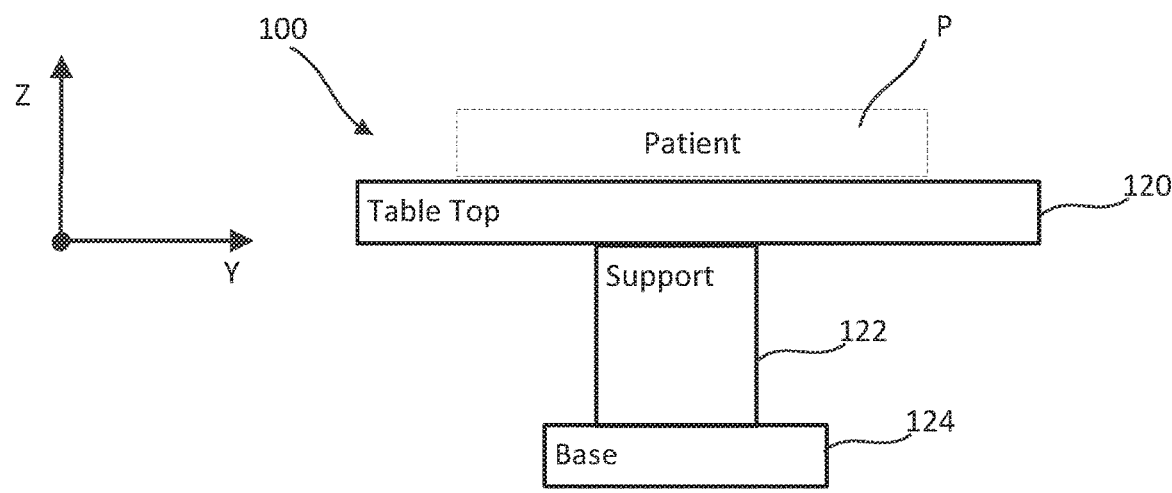
FIGS. 1A and 1B are a schematic side view and a schematic top view, respectively, of a surgical table, according to an embodiment.
Figure 1B:
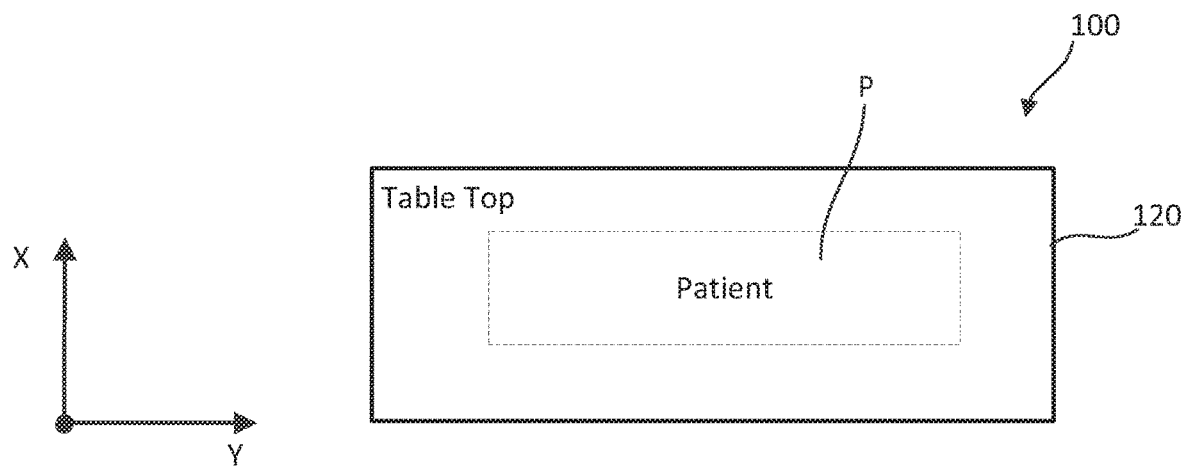

As shown schematically in FIGS. 1A-1B, a surgical table 100 includes a tabletop 120, a table support 122 and a table base 124. The tabletop 120 has an upper surface on which a patient P can be disposed during a surgical procedure, as shown schematically in FIG. 1A. The tabletop 120 is disposed on the support 122, which can be, for example, a pedestal, at a suitable height above the floor. The support 122 (also referred to herein as a pedestal) may provide for movement of the tabletop 120 in a desired number of degrees of freedom, such as translation in the vertical or Z-direction (height above the floor), the horizontal Y-direction (e.g., along the longitudinal axis of the table), and/or the horizontal X-direction (e.g., along the lateral axis of the table), and/or rotation about Z-, Y-, and/or X-axes. The tabletop 120 may also include multiple sections that are movable relative to each other along/about any suitable axes, e.g., separate sections for each of the torso, one or both legs, and/or one or both arms, and a head support section. Movement of the tabletop 120 and/or its constituent sections may be performed manually, driven by motors, controlled remotely, or through any other suitable means. The support 122 for the tabletop 120 may be mounted to the base 124, which can be fixed to the floor of the operating room, or can be movable relative to the floor, e.g., by use of wheels on the base 124. In some embodiments, the height of the support 122 can be adjusted, which together with, for example, the motion (e.g., axial (longitudinal) or lateral motion) of the tabletop 120, can allow for the tabletop 120 to be positioned at a desired surgical site at a certain height above the floor (e.g., to allow surgeon access) and a certain distance from the support 120. This also can allow robotic arms (e.g., arms 130 discussed below) coupled to the table 100 to reach a desired treatment target on a patient P disposed on the tabletop 120.

In a robotically-assisted surgical procedure, one or more robotic arms 130 (shown schematically in FIGS. 1C and 1D) can be disposed in a desired operative position relative to a patient disposed on the tabletop 120 of the surgical table 100 (also referred to herein as "table"). The robotic arm(s) can be used to perform a surgical procedure on a patient disposed on the surgical table 100. In particular, the distal end of each robotic arm can be disposed in a desired operative position so that a medical instrument coupled to the distal end of the robotic arm can perform a desired function.

Figure 1C:
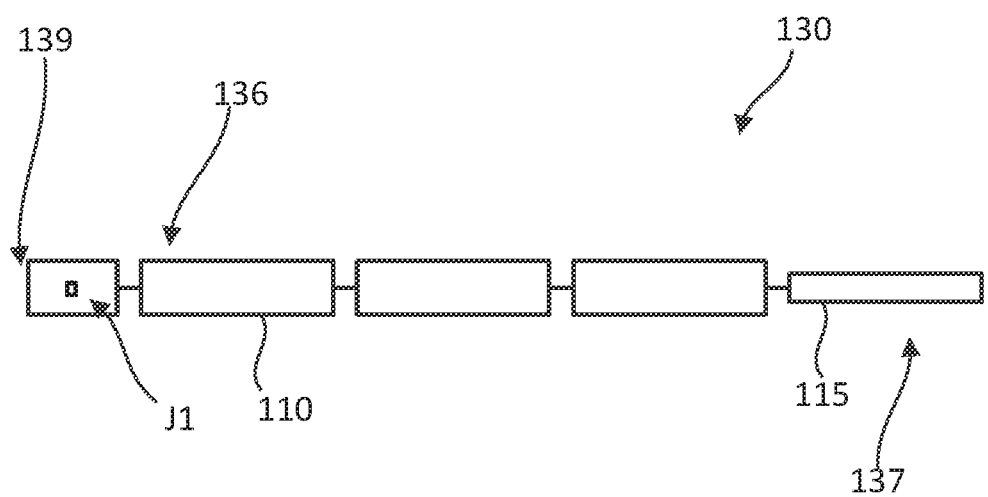
FIG. 1C is a schematic side view of a robotic arm, according to an embodiment, shown in an extended or use configuration.
Figure 1D:
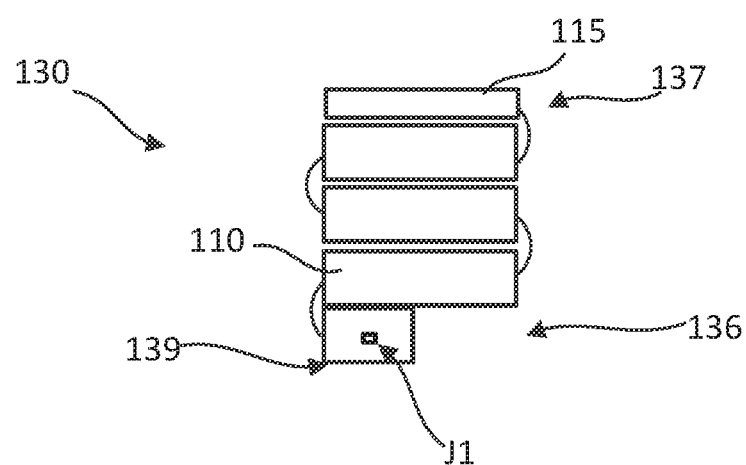
FIG. 1D is a schematic side view of the robotic arm of FIG. 1C, shown in a collapsed or folded configuration.

As shown schematically in FIGS. 1C and 1D, each robotic arm 130 can include a distal end portion 137 and a proximal end portion 136. The distal end portion 137 (also referred to herein as "operating end") can include or have coupled thereto a medical instrument or tool 115. The proximal end portion 136 (also referred to herein as the "mounting end portion" or "mounting end") can include the coupling portion to allow the robotic arm 130 to be coupled to the table 100. The robotic arm 130 can include two or more link members or segments 110 coupled together at joints that can provide for translation along and/or rotation about one or more of the X, Y and/or Z axes (shown, for example, in FIGS. 1A and 1B). The coupling portion of the robotic arm 130 can include a coupling mechanism 139. The coupling mechanism 139 can be disposed at the mounting end 136 of the arm 130 and may be coupled to a segment 110 or incorporated within a segment 110. The robotic arm 130 also includes a target joint J1 disposed at or near the mounting end 136 of the robotic arm 130 that can be included within the coupling mechanism 139 and/or the coupling portion or can be disposed on a link or segment 110 of the robotic arm 130 that is coupled to the coupling portion. The target joint J1 can be operable to allow a distal segment of the robotic arm 130 to pivot and/or rotate relative to the table 100. The robotic arm 130 can be moved between various extended configurations for use during a surgical procedure, such as shown in FIG. 1C, and various folded or collapsed configurations for storage when not in use, such as shown in FIG. 1D.

Figure 2A:
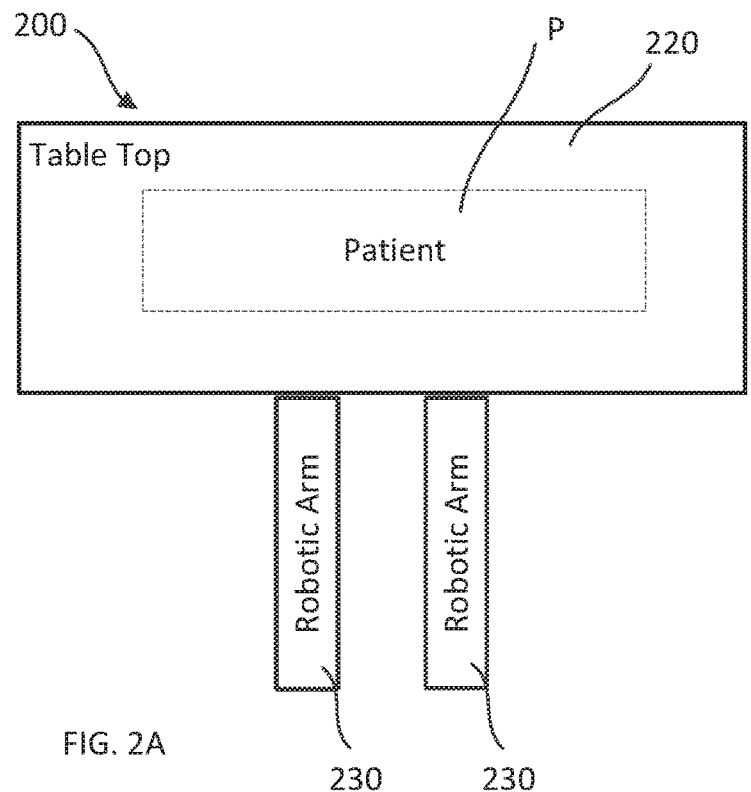
FIG. 2A is a schematic top view of a surgical table with robotic arms coupled thereto, according to an embodiment.
Figure 2B:
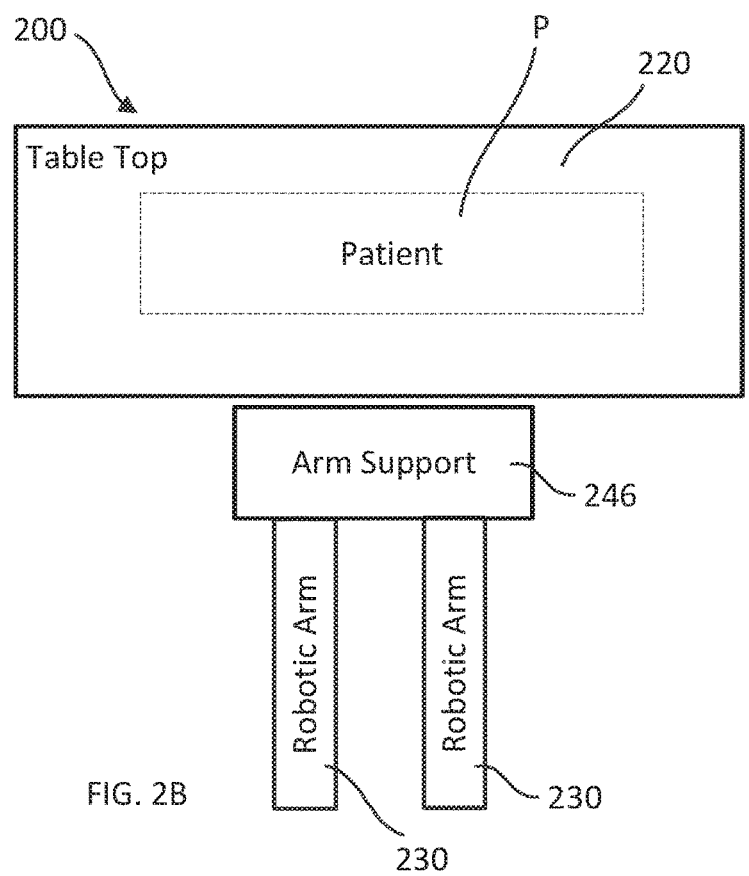
FIG. 2B is a schematic top view of a surgical table with robotic arms and an arm adapter coupled thereto, according to an embodiment.

FIGS. 2A-2B illustrate various embodiments describing apparatus and methods for transporting, delivering, and securing a robotic arm to a surgical table. As described above and in accordance with various embodiments disclosed in more detail below, a robotic arm for use in performing a surgical procedure may be releasably coupled to a surgical table. In some embodiments, robotic arms can be coupled at a fixed location on the table or can be coupled such that the robotic arms can be movable to multiple locations relative to the tabletop. For example, as shown schematically in FIG. 2A, robotic arms 230 can be coupled to a tabletop 220 of a surgical table 200. The surgical table 200 can be the same or similar in structure and function to the surgical table 100 described above. For example, the tabletop 220 has an upper surface on which a patient P can be disposed during a surgical procedure. In some embodiments, the robotic arms 230 can be permanently or releasably coupled, in a fixed or movable location, to an arm support (also referred to herein as an arm adapter) that is coupled to or separate from the surgical table. For example, as shown schematically in FIG. 2B, an arm adapter 246 can be coupled to or separate from but engageable with or coupleable to the tabletop 220. The robotic arms 230 can be coupled to the arm adapter 246.

In preparation for a robotically-assisted surgical procedure in which one or more robotic arms are releasably coupled to the surgical table and/or to an arm adapter, as described with respect to FIGS. 2A and 2B, each robotic arm may be delivered and connected to the surgical table and/or the arm adapter via an arm cart. An arm cart can be configured to support one or more robotic arms. Arm carts, according to various embodiments are described in further detail below.

FIGS. 3A-3G depict various configurations of an arm cart 350, according to an embodiment. The arm cart 350 is configured to contain one or more robotic arms 330 or cartridges containing robotic arms. Although two robotic arms 330 are shown, the arm cart 350 can be configured to contain, transport, and/or deliver any suitable number of robotic arms 330, such as, for example, one robotic arm, three robotic arms, or four robotic arms.

Figure 3A:
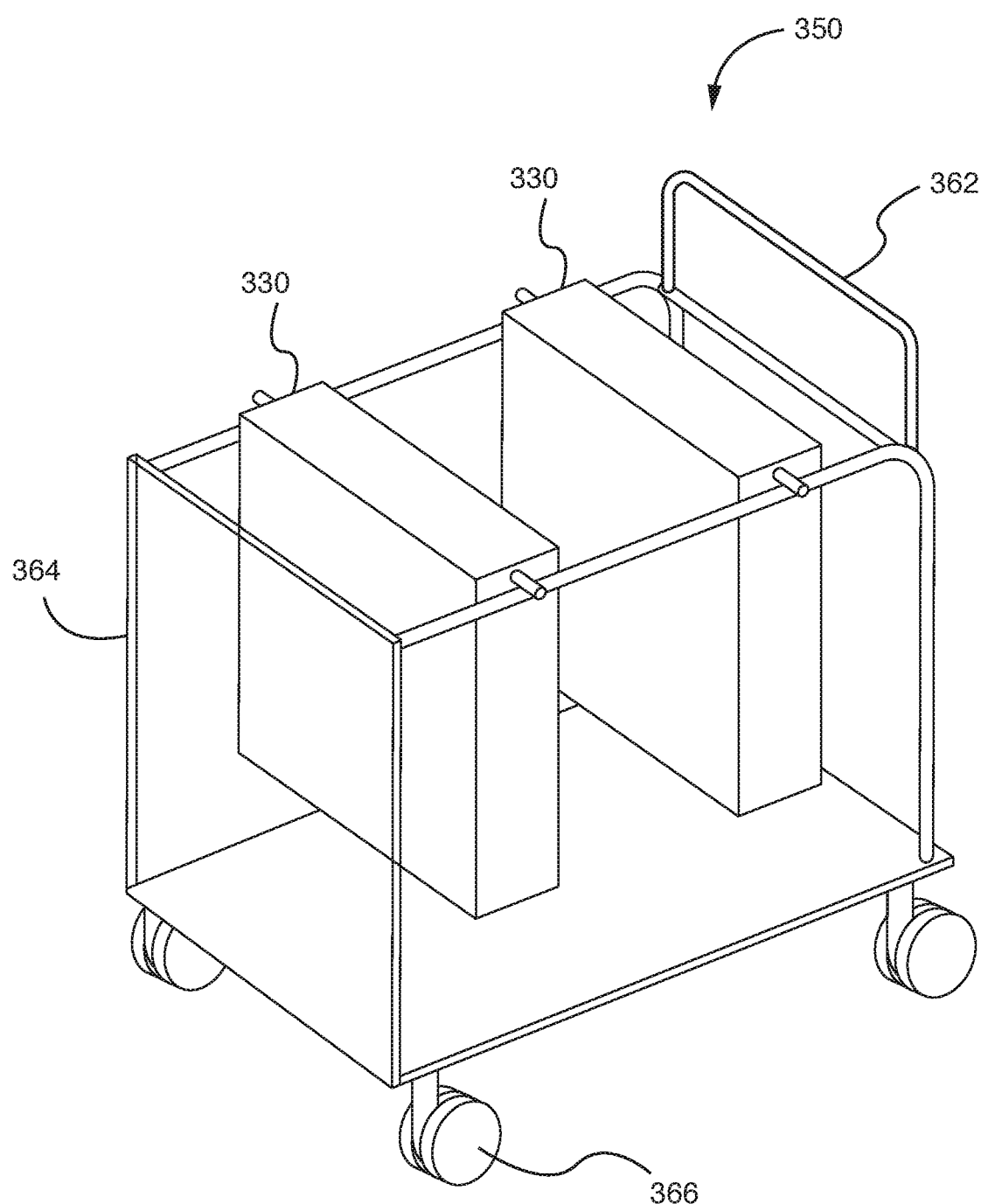
FIG. 3A is a schematic illustration of an arm cart, according to an embodiment.

As shown, in FIG. 3A, the arm cart 350 includes wheels 366 and a front portion 364 and a back portion 362. The arm cart 350 can be intended to be pushed and/or pulled from the back portion 362; for example, the back portion 362 can include a handle 362. The arm cart 350 can be operable to store the robotic arms 330 when not in use and/or transport the robotic arms 330 between storage and surgical tables, such as surgical table 100. As described in further detail herein, the front portion 364 of the arm cart 350 can be positioned adjacent to the surgical table (e.g., the front portion 364 can be disposed between the back portion 362 and the surgical table), and one or more of the robotic arms 330 can be transferred from the arm cart 350 to the surgical table.

As shown in FIGS. 3B-3G, a first robotic arm 330A and a second robotic arm 330B are slideably disposed within the arm cart 350. Similarly stated, the first robotic arm 330A and the second robotic arm 330B are movable in an X-direction, that is, between the front portion 364 and the back portion 362 of the arm cart 330. Although FIGS. 3B-3G illustrate an X-axis, it should be understood that this X-axis, is not necessarily identical to the X-axis depicted in FIG. 1B. Similarly stated, the X-direction in FIGS. 3B-3G can represent any suitable horizontal direction. In addition or alternatively, first robotic arm 330A and/or the second robotic arm 330B can also be rotatably disposed within the arm cart 350.

The arm cart 350 can support the robotic arms 330 in a variety of configurations. In some embodiments and/or configuration, the arm cart 350 can support the robotic arms 330 such that the center of gravity of the robotic arm 330A is below one or more arm support structure locations (e.g., cradles) of the arm cart 350 such that the stability of the robotic arm 330A and the arm cart 350 is increased. In some embodiments, the arm cart 350 can support the robotic arms 330 such that the arm cart 350 bears most or all of the weight of the robotic arms 330 and a coupling mechanism (not shown) of the robotic arms 330 can be manually manipulated by a user without the user bearing most or all of the weight of the robotic arm. For example, the robotic arms 330 can be suspended from a structure of the arm cart 350 or rested on a structure of the arm cart 350. In some embodiments, the arm cart 350 can be configured to secure the robotic arms 330 to the arm cart 350.

The arm cart 350 can include an arm container 352 and a base 354. The arm container 352 is configured to support, protect, and/or promote sterility for one or more robotic arms 330 (e.g., the first robotic arm 330A and the optional second robotic arm 330B) during storage and/or transportation of the robotic arms 330, for example, from a storage area to the operating area, and during transfer of the one or more robotic arms 330 from the arm cart 350 to a surgical table for use during the surgical procedure. While the one or more robotic arms 330 are stored and/or transported by the arm cart 350, the one or more robotic arms 330 can be mostly, substantially completely, or completely maintained within the footprint of the arm cart 350 such that the one or more robotic arms 330 will be less likely to be accidentally bumped or damaged. In some embodiments, the arm container 352 can be structured as a vertically-extending protection frame that, in combination with the base 354, defines a space for storing the one or more robotic arms 330. In some embodiments, when the one or more robotic arms 330 are stored within the arm cart 350, the robotic arms can be maintained within the perimeter of the base 354, but may extend beyond the perimeter of the arm container 352.

The base 354 can be configured to support the arm container 352 and provide transportation of the arm cart 350 to the surgical area. The base 354 can include any suitable means for movement of the arm cart 350 relative to the floor. For example, the base 354 can include wheels 366 such that a medical provider can push/pull the arm cart to/from the operating area.

The arm cart 350 can include features that assist in aligning the one or more robotic arms 330 for transfer to the surgical table along the X, Y, and/or Z axes and/or rotationally about the X, Y, and/or Z axes. For example, as described above, the base 354 can include any suitable means for movement of the arm cart 350 such that the arm cart 350 can be moved along the X axis and/or the Y axis relative to the surgical table. Additionally, the arm cart 350 can include any suitable means for adjusting the height of the arm cart 350 and/or the one or more robotic arms 330 such that the height of the one or more robotic arms 330 can be adjusted relative to the surgical table. Thus, the arm cart 350 can move the one or more robotic arms 330 along the X, Y, and/or Z axes and/or rotationally about the X, Y, and/or Z axes such that a coupling portion of at least one of the one or more robotic arms 330 can be aligned for engagement with a mating coupling portion on a table or a table adapter.

In some embodiments, the arm cart 350 houses the one or more robotic arms 330 such that a line of sight can be maintained from the operator of the arm cart 350 to the portion of the surgical table to which the one or more robotic arms 330 are to be transferred during the approach of the arm cart 350 to the surgical table and the transfer of the one or more robotic arms 330 to the surgical table.

The one or more robotic arms 330 can be docked and/or mounted to the surgical table using a variety of different types of coupling and/or mounting methods and mechanisms. The arm cart 350 can employ corresponding coupling methods and mechanisms to provide efficient transfer of the robotic arms 330 from the arm cart 350 to any suitable location on the surgical table and/or an arms support associated with the surgical table. In this manner, the arm cart 350 and the surgical table can include a common interface such that the robotic arms 330 can be efficiently and repeatedly coupled to and/or removed from the surgical table and the arm cart 350.

Figure 3B:
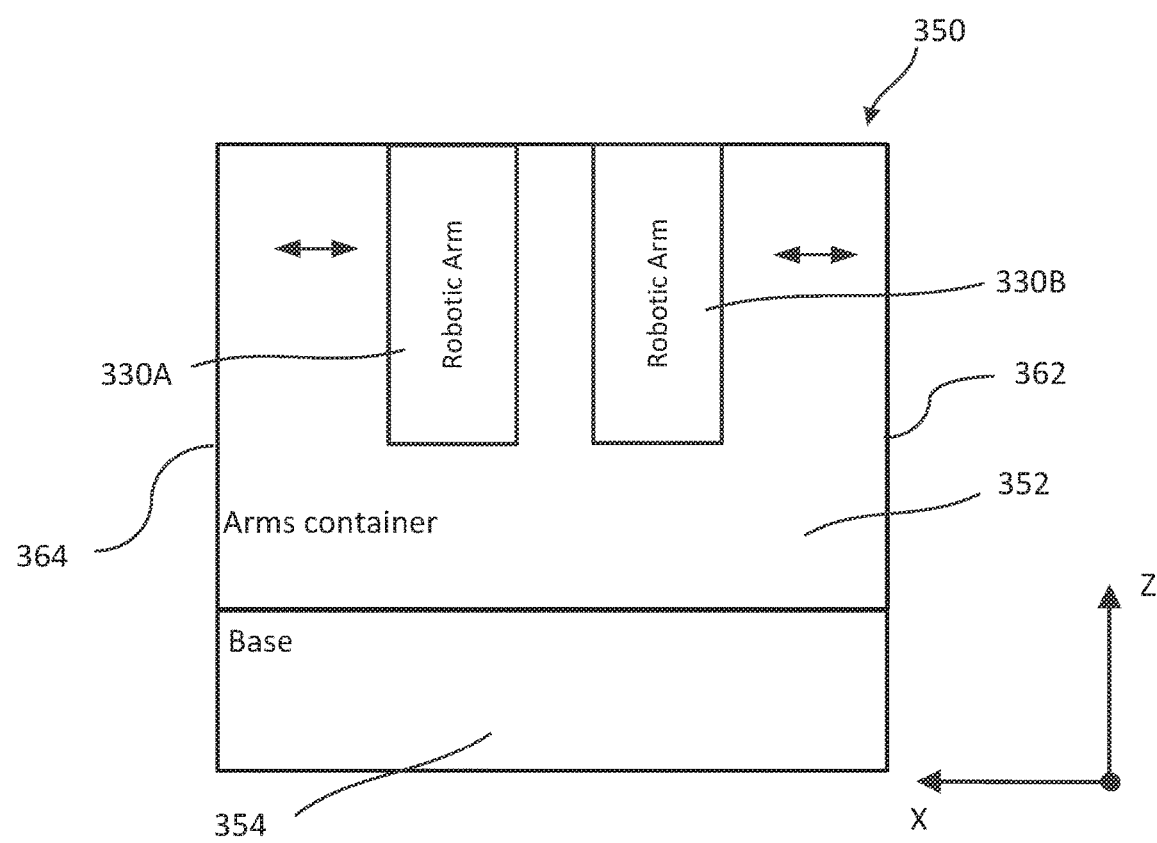
FIGS. 3B-3G are schematic side views of an arm cart having robotic arms in various configurations, according to an embodiment.
Figure 3C:
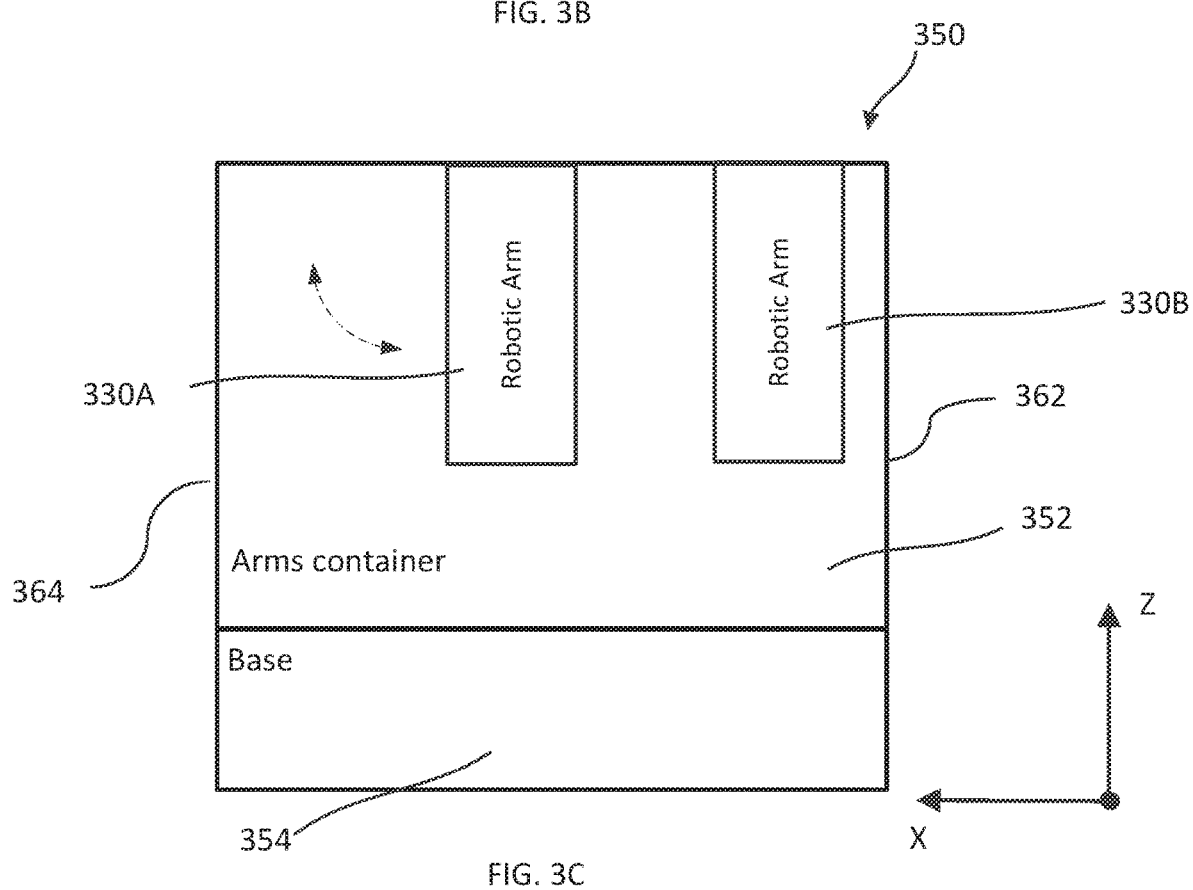

FIGS. 3B-3G illustrate an example sequence of configurations suitable for transferring the first robotic arm 330A from the arm cart 350 to surgical table 380, which can be structurally and/or functionally similar to surgical table 100. As shown in FIGS. 3B and 3C, each of the first robotic arm 330A and the second robotic arm 330B is in a storage position and can be moved in the X-direction within the arm container 352. As shown in FIG. 3B-3E, the second robotic arm 330B can be moved towards the back portion 362 of the arm cart 350 and the first robotic arm 330A can be moved towards the middle to provide sufficient clearance for the first robotic arm 330A to pivot from the storage position about the Y-axis in the Z-direction to a deployment position, in which all or at least a portion of the first robotic arm 330A is disposed outside of the arm container 352.

Figure 3D:
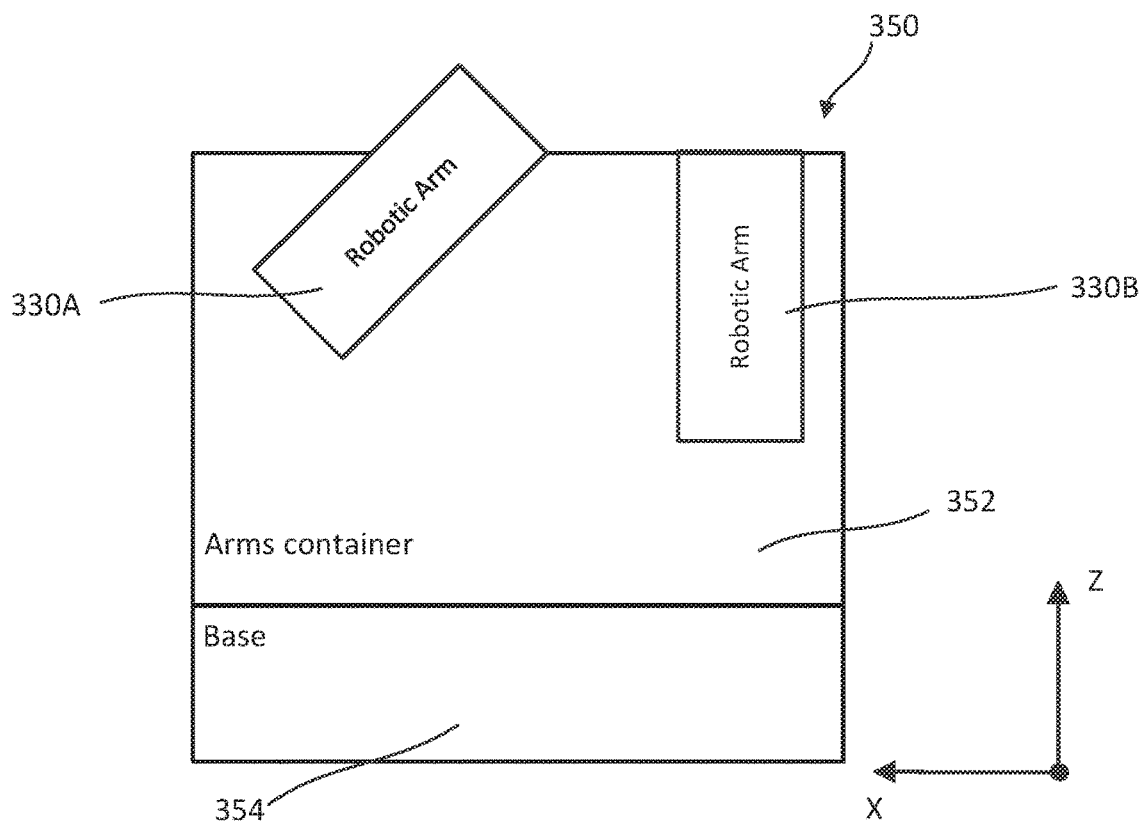
Figure 3E:
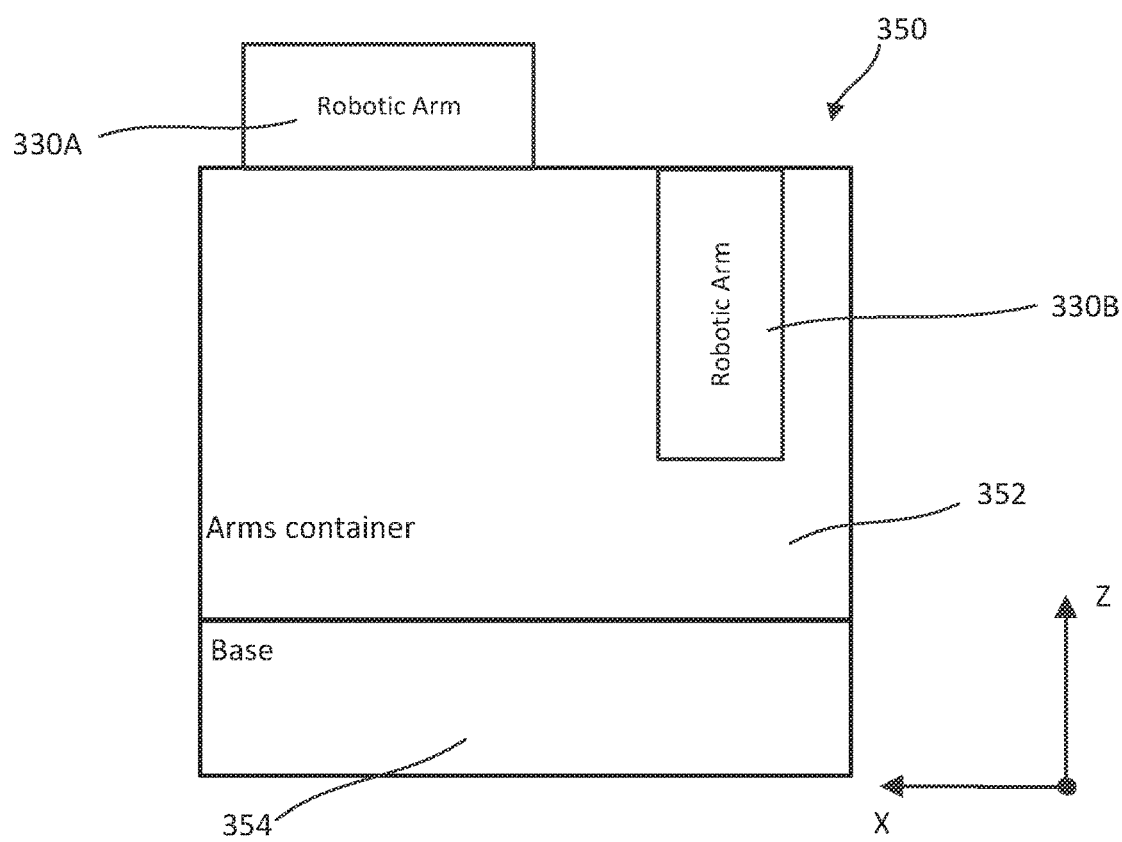
Figure 3F:
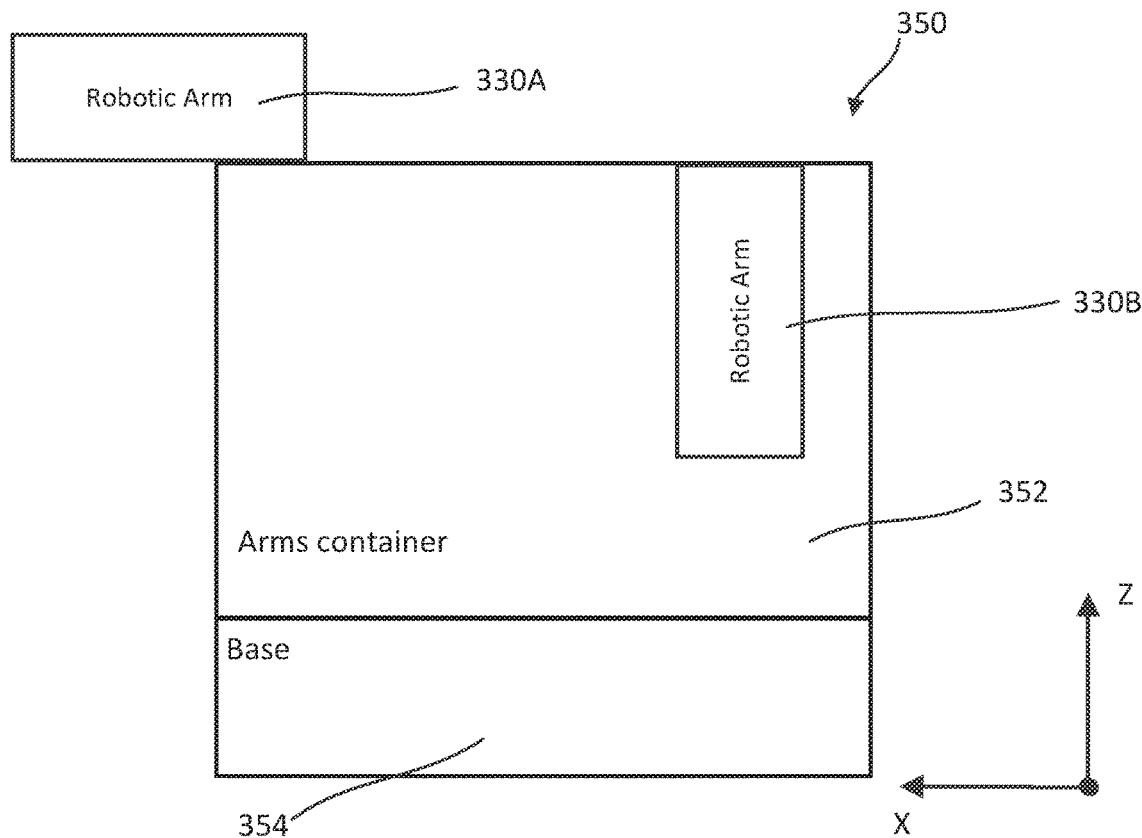
Figure 3G:
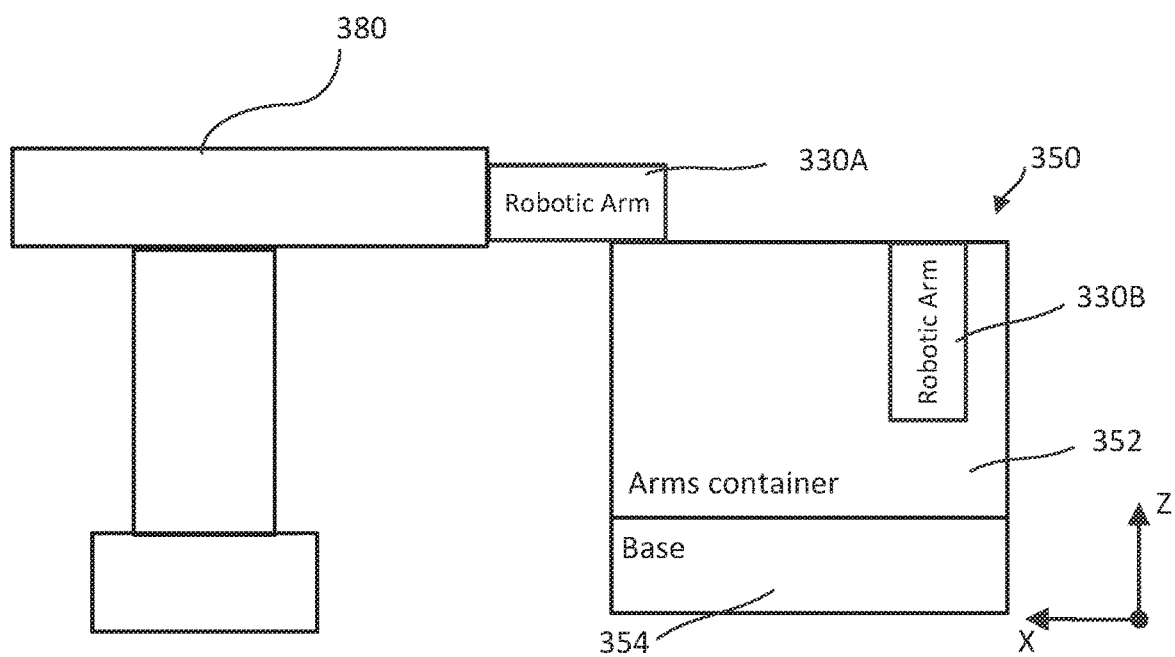

FIGS. 3F and 3G depict the first robotic arm 330A outside of arm container 352 sliding in the X-direction. When extended, for example, as shown in FIG. 3G, the first robotic arm 330A can mate with or otherwise be coupled to the surgical table 380. In some embodiments, the base 354 of the surgical table can be operable to adjust the height of the arm cart 330 and/or interface with a base of the surgical table 380 to align or otherwise facilitate the transfer of the first robotic arm 330A to the surgical table 380.

In some embodiments, the first robotic arm 330A can unfold or otherwise alter its configuration after being coupled to the surgical table 380. Once coupled to the surgical table, the first robotic arm 330A can be controlled via the surgical table 380 and operable to move and/or articulate in any suitable manner.

In some instances after the first robotic arm 330A is coupled to the surgical table 380 the arm cart 350 can be moved away from the surgical table 380 and set aside until a surgical procedure is complete. Then, the process shown in FIGS. 3B-3G can be reversed and the first robotic arm 330A placed back within the arm container 352 of the arm cart 350.

In some instances, after the first robotic arm 330A is coupled to the surgical table 380, the arm cart 350 can be moved to another location and the second robotic arm 330B can be transferred to the surgical table 380 via a similar technique. In some instances, the arm cart 350 can be configured such that the first robotic arm 330A can be transferred to the surgical table 380 when the front portion 364 is adjacent to the surgical table 380 and the second robotic arm 330B can be transferred to the surgical table 380 when the back portion 362 is adjacent to the surgical table. In some embodiments, the first robotic arm 330A and the second robotic arm 330B can be operable to pivot in opposite direction. In other embodiments, one or both of the first robotic arm 330A and the second robotic arm 330B can be operable to pivot in any direction.

Although the robotic arms 330 are shown as movable in the X-direction, it should be understood that in other embodiments robotic arms 330 can be movable in the Y-direction. For example, the arm cart 350 can be operable to couple a robotic arm via a left or right portion of the arm cart 350 (e.g., rather than via the front portion 364 and/or the back portion 362). For example, in some such embodiments, the robotic arms 330 can be in a square arrangement within the arm container 352. In some such embodiments, at least one robotic arm can be operable to be coupled to the surgical table 380 via the front portion 364 and/or the back portion 362 of the arm cart 350, while at least one other robotic arm can be operable to be coupled to the surgical table 380 via the right portion and/or the left portion of the arm cart.

Although FIGS. 3B-3G depict the first robotic arm 330A being positioned in front of the second robotic arm 330B and coupled to the surgical table 380 via the front portion 364 of the arm cart 350, it should be understood that in other instances, the second robotic arm 330B, which is shown positioned to the rear of the first robotic arm 330A can be selected and coupled to the surgical table 380 prior to the first robotic arm 330A being coupled to the surgical table 380. For example, in some embodiments, the second robotic arm 330B can be coupled to the surgical table via the rear portion 362 of the surgical cart 350 while the first robotic arm 330A remains in a storage position. In other embodiments, the second robotic arm 330B can slide over the first robotic arm and be coupled to the surgical table 380 via the front portion 364 of the surgical cart, while the first robotic arm 330A remains in the storage position.

Figure 4A:
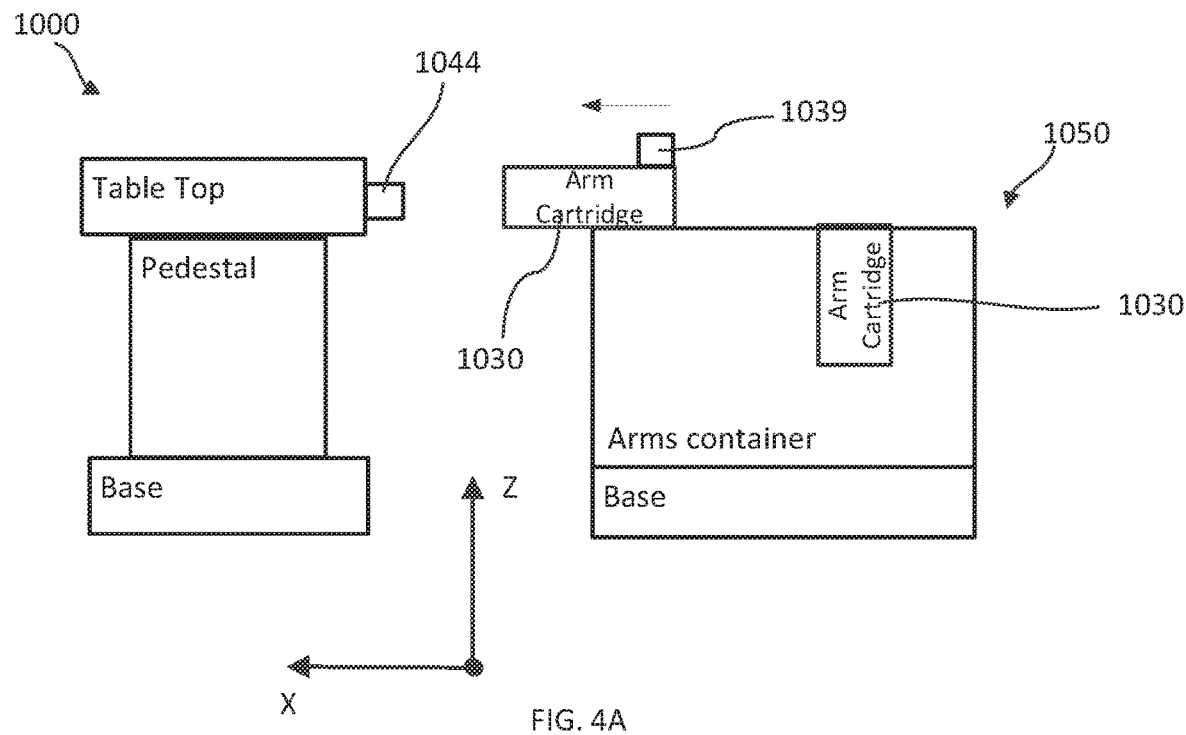
FIGS. 4A and 4B are schematic illustrations of an arm cart having robotic arms in two configurations, according to an embodiment.
Figure 4B:
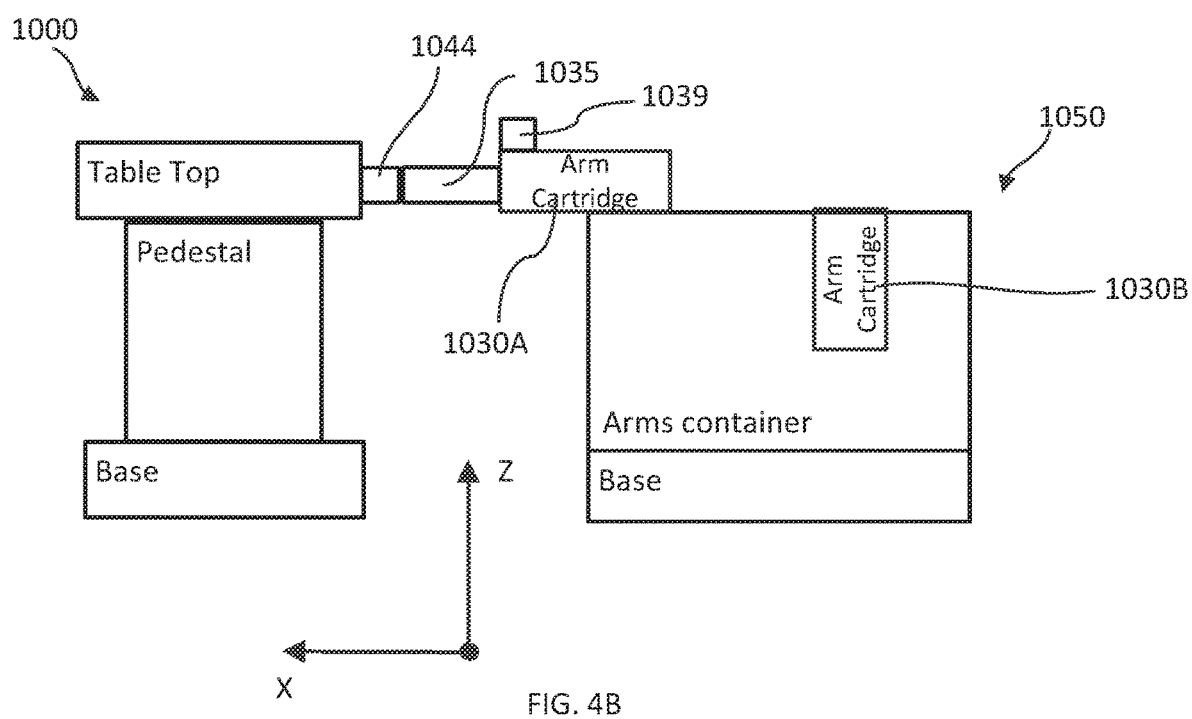

FIGS. 4A and 4B depict an arm cart 1050 and a surgical table 1000 according to an embodiment similar to that shown and described above with reference to FIGS. 3A-3G. Each of the robotic arms 1035 of FIGS. 4A and 4B is disposed within a respective arm cartridge 1030. The arm cartridges 1030A and 1030B can be moved within the arms cart 1050 in a manner similar to the movements of the robotic arms 330 described above with reference to FIGS. 3A-3G. As shown in FIG. 4A, arm cartridge 1030A is at least partially disposed outside the arm cart 1050. The arm cartridge 1030A may include an actuator 1039 that can be moved to eject the robotic arm 1035 from the arm cartridge 1030A. In some embodiments the actuator 1039 can be moved by hand to eject the robotic arm 1035. In other embodiments the robotic arm 1035 can be automatically ejected from the arm cartridge 1030A, for example, when the arm cart 1050 detects it is properly aligned with the surgical table 1000 and/or when a user actuates a motor or other suitable mechanism. In embodiments in which robotic arm 1035 is automatically ejected from the arm cartridge 1030A (e.g., without a user applying a physical force to the actuator 1039), the arm cartridge 1030A may not include actuator 1039. In other embodiments, the robotic arm 1035 can be coupled to the surgical table 1000 while the robotic arm 1035 is partially and/or completely disposed within the arm cartridge 1030A; the robotic arm 1035 can be withdrawn from the arm cartridge 1030A by moving the arm cart 1050 away from the surgical table 1000.

As shown in FIG. 4B, the robotic arm 1035 has been ejected from the arm cartridge 1030A, and is coupled to the surgical table 1000. The surgical table includes a coupling mechanism 1044 configured to receive the robotic arm 1035. In some embodiments, the surgical arm 1035 can be operable to rotate about the coupling mechanism 1044. The surgical arm 1035 can also receive power and/or control signals via the coupling mechanism 1044.

Figure 9:
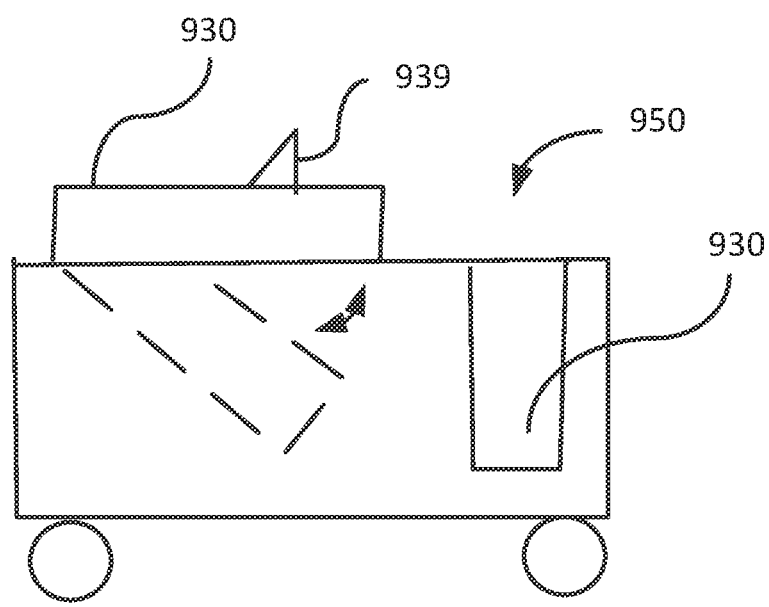
FIG. 9 is a schematic illustration of an arm cart, according to an embodiment.

In addition or alternatively, the arm cartridge 1030 can include a latch, such as latch 939 shown in FIG. 9. FIG. 9 illustrates an arm cart 950 and an arm cartridge 930, each of which can be structurally and/or functionally similar to the arm cart 1050 and/or the arm cartridge 1030, respectively. When the latch 939 is actuated, a robotic arm (not shown in FIG. 9) disposed within the arm cartridge 930 can be held in a fixed position. When the latch is deactivated (e.g., by depressing the latch or via electronic means), the robotic arm can be free to move within the arm cartridge 930, for example such that the robotic arm can be transferred to a surgical table. FIG. 9 further depicts an embodiment in which the arm cartridge 930 is operable to pivot in a direction opposite of that shown in FIGS. 2A-3G.

Figure 5:
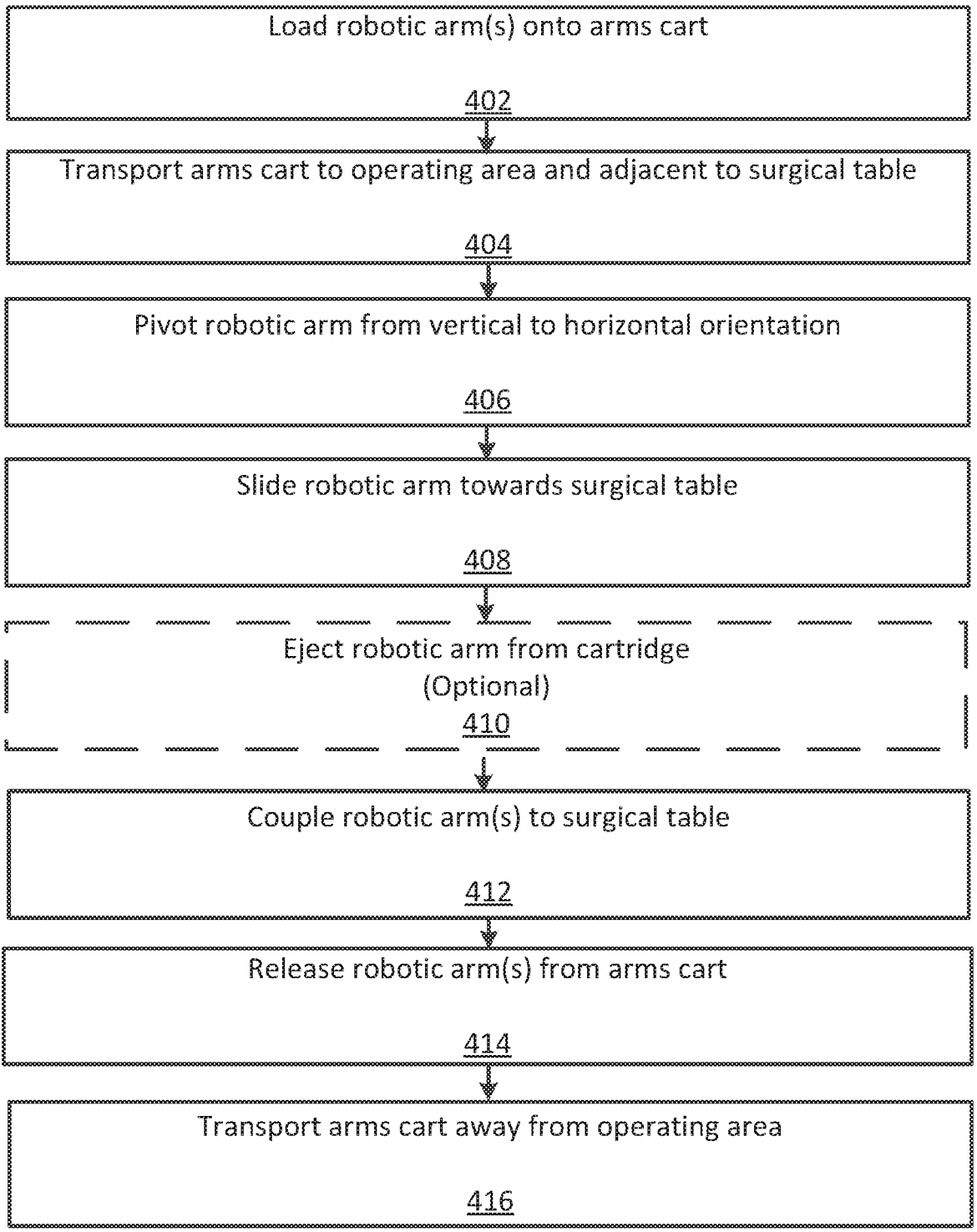
FIG. 5 is a flowchart of a method of transporting and transferring surgical robotic arms to a surgical table using a surgical robotic arm cart, according to an embodiment.

FIG. 5 is a flowchart of a method 400 of transporting and transferring surgical robotic arms to a surgical table using a surgical robotic arm cart, such as the arm carts 350 and/or 1050 shown and described above. The method 400 includes loading one or more robotic arms onto an arm cart at 402. For example the one or more robotic arms can be folded into a configuration suitable for transport and/or loaded into an arm cartridge (e.g., arm cartridges 1030). Similarly stated the one or more robotic arms and/or arm cartridges can be releasably coupled to an arm support of the arm cart. The robotic arms can be disposed in a vertical configuration within the arm cart, for example, as shown in FIGS. 3A-3C. The arm support can be coupled to a base of the arm cart to support the one or more robotic arms above the base. The base can be freely movable on a support surface. The arm cart is then transported to an operating area and adjacent to a surgical table, at 404.

The robotic arm can be pivoted from a vertical orientation to a horizontal configuration, at 406, for example, as shown in FIGS. 3C-3E. The robotic arm can be slid towards the surgical table, at 408, for example, as shown in FIGS. 3E and 3F. In embodiments in which the robotic arm is disposed within a cartridge, the robotic arm can be ejected the robotic arm from the cartridge, at 410, for example, as shown in FIGS. 4A and 4B. The robotic arm can be coupled to the surgical table, at 412. The robotic arm can then be released from the arm cart, at 414, and the arm cart is transported away from the operating area, at 416.

In some embodiments, if a second robotic arm has been loaded onto the arm cart, the arm cart can couple a first robotic arm to the surgical table, release the first robotic arm from the arm cart, and then be transported to a location adjacent another portion of the surgical table. The second robotic arm can then be coupled to the surgical table via, by repeating steps 406-414.

FIGS. 6A and 6B are schematic front views of an arm cart 650 in two configurations, according to an embodiment. FIG. 6C is a schematic side view of the arm cart 650 in the configuration shown in FIG. 6B. The arm cart 650 can include an arm container 652 and a base 654, which can be structurally and/or functionally similar to the arm container 352 and/or the base 354, respectively as shown and described above, The arm cart 650 includes multiple robotic arms 630 coupled to a rotary mechanism 670. As shown, the rotary mechanism 670 is pentagonal in shape and configured to receive four robotic arms 630, (a first robotic arm 630A, a second robotic arm 630B, a third robotic arm 630C, and a fourth robotic arm 630D), but it should be understood that the rotary mechanism 670 can be any suitable shape and configured to receive any suitable number of robotic arms 630. The rotary mechanism 670 can be operable to move robotic arms 630 and/or portions of the rotary mechanism configured to receive robotic arms into a loading/unloading region 635. Robotic arms 630 can be loaded and/or unloaded from the arm cart 650 via the loading/unloading region 635.

FIG. 6A depicts the arm cart 650 in a storage configuration in which all four of the robotic arms 630 are disposed within the arm container 652 portion of the arms cart 650. Similarly stated, in the storage configuration no robotic arms 650 and/or portions of the rotary mechanism 670 operable to receive robotic arms may be disposed in the loading/unloading region 635. The rotary mechanism 670 can be turned (e.g., manually and/or by a drive mechanism, which may be mechanical, electrical, hydraulic, etc.), simultaneously moving all the robotic arms 630 and such that the first robotic arm 630A is moved from a storage position to a deployment position in the loading/unloading region 635, as shown in FIG. 6B. In some embodiments the first robotic arm 630A is partially or completely outside the arm container 652 in the deployment position. FIG. 6C is a side view of the arm cart 650 in the configuration shown in FIG. 6B. For ease of illustration, the second robotic arm 630B and the fourth robotic arm 630D are not shown in FIG. 6C.

Figure 6D:
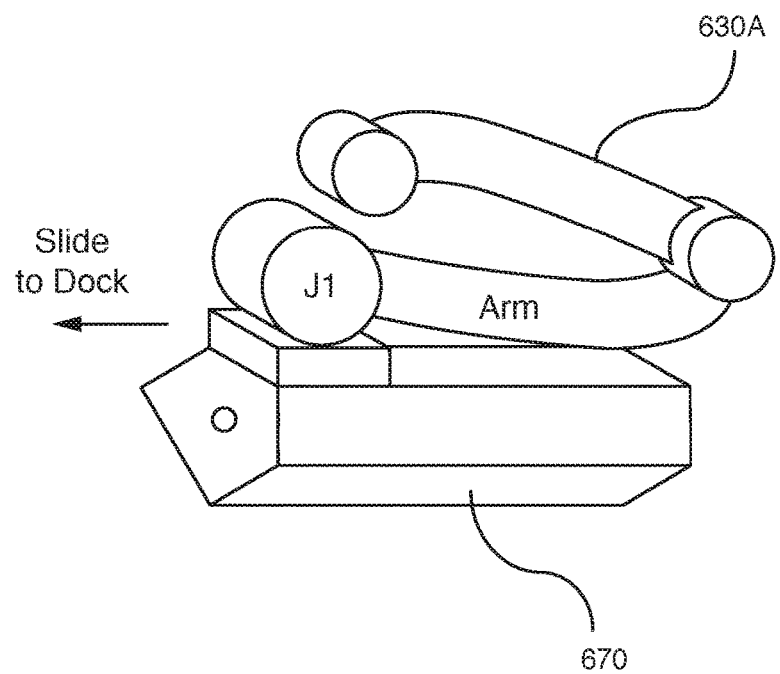
FIG. 6D is a schematic illustration of the rotary mechanism and a robotic arm of FIGS. 6A-6C.

FIG. 6D is a schematic illustration of the first robotic arm 630A coupled to the rotary mechanism 670. The first robotic arm 630A and remaining robotic arms 630 (not shown in FIG. 6D) can be slidably coupled to the rotary mechanism 670. In some embodiments, the robotic arms 630 can be releasably latched to the rotary mechanism, such that the robotic arms are fixed relative to the rotary mechanism until the latch is released. In this way, when a robotic arm 630 is disposed in the loading/unloading region 635, that robotic arm 630 can be (optionally unlatched and) slid horizontally in a forward (or backward) direction such that that robotic arm 630 can be received by a surgical table 680 as illustrated, for example, in FIG. 6E. As shown in FIG. 6D, the robotic arm 630 includes a target joint J1, which can be coupled to the surgical table 680 as discussed above. Once the robotic arm 630 is coupled to the surgical table 680, the robotic arm 630 can decoupled from the rotary mechanism 670 and the arm cart 650 can be withdrawn.

Figure 6E:
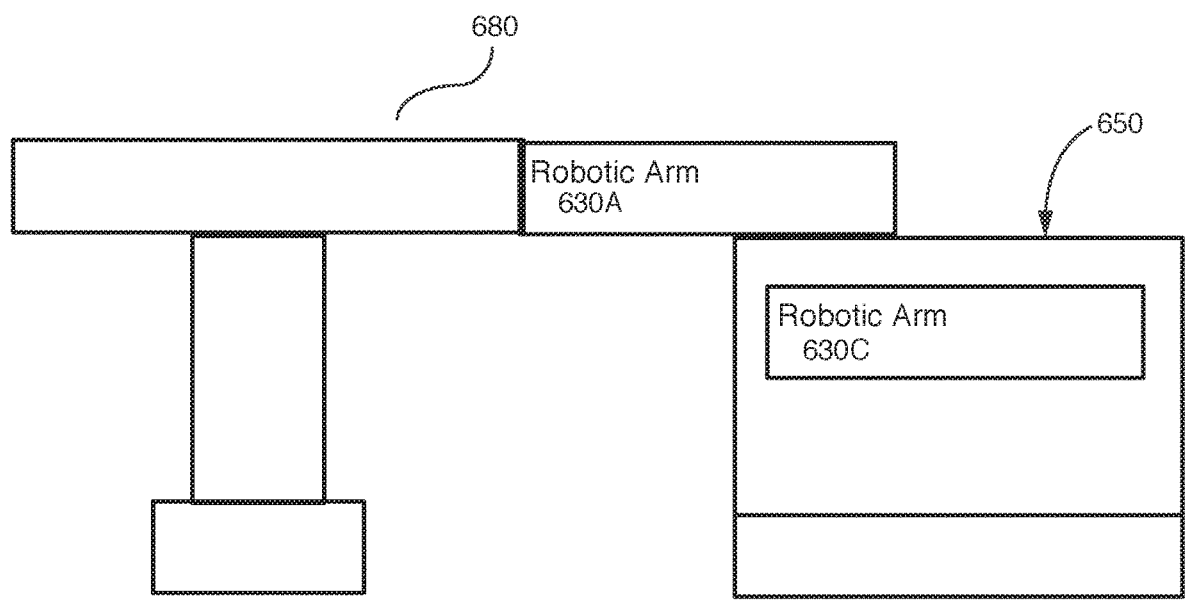
FIG. 6E is a schematic illustration of the arm cart of FIGS. 6A-6D showing a surgical table.

Although FIGS. 6B, 6C, and 6E show and describe the first robotic arm 630A being coupled to the surgical table 680, it should be understood that any of robotic arms 630 disposed within the arm cart 650 can be selected and coupled to the surgical table 680 by rotating the rotary mechanism 670 to the appropriate position. For example, in some embodiments, multiple robotic arms 630 can be coupled to one surgical table 680 for a procedure.

FIGS. 6B, 6C, and 6E also show and describe a robotic arm 630 being disposed outside of the arm container 652 when that robotic arms 630 is configured to be coupled to the surgical table 680. Similarly stated, FIGS. 6A-6C depict the loading/unloading region 635 being at least partially disposed outside of the arm container 652. It should be understood, however, that in other embodiments, the arm cart 650 can include a port or other similar opening through which the robotic arms 630 can be slid. In such an embodiment, the rotary mechanism 670 can be turned such that the desired robotic arm 630 is aligned with the port, and that robotic arm 630 can be slid through the opening without that robotic arm having previously moved outside of the arm container 652.

Figure 6F:
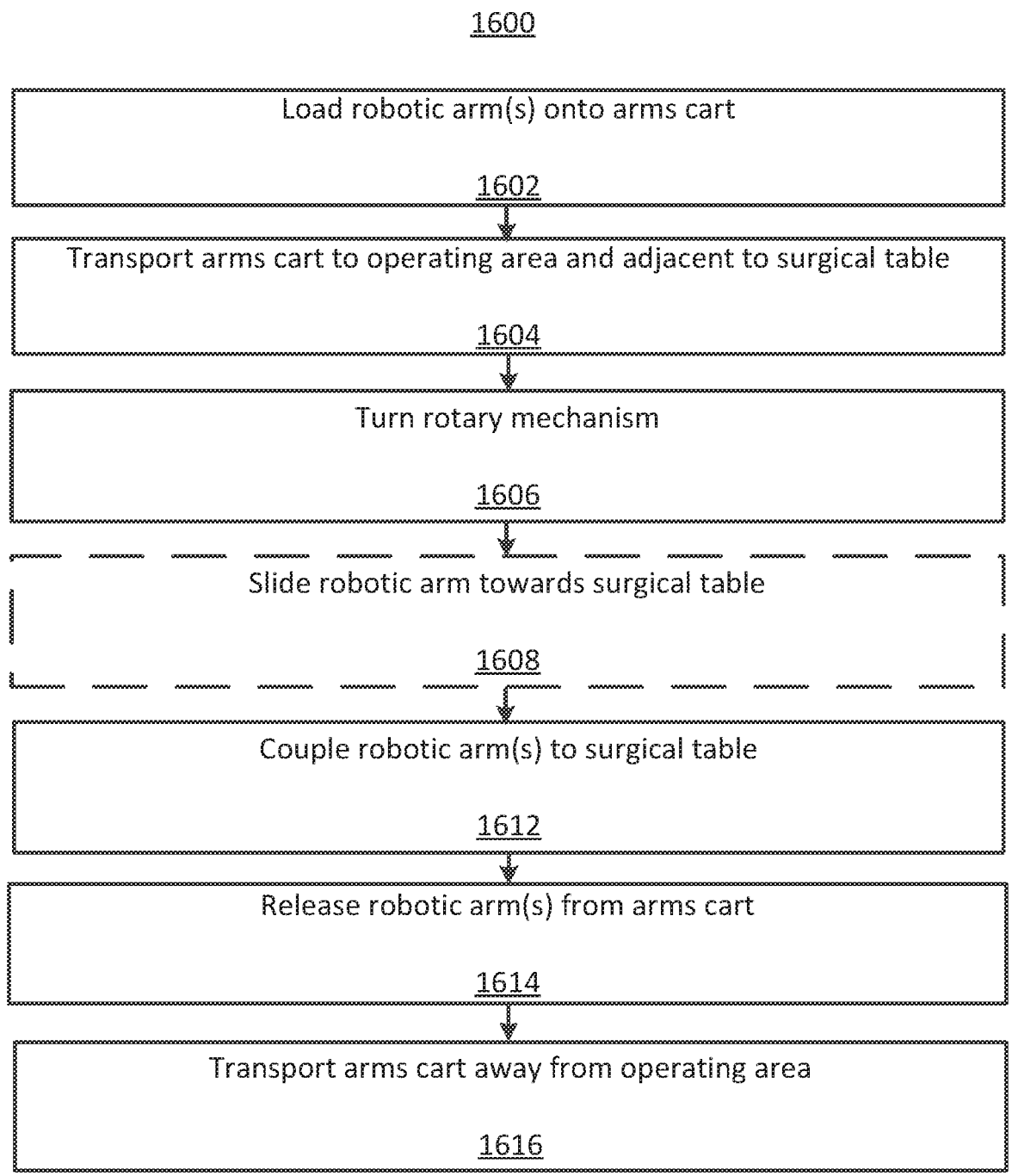
FIG. 6F is a flowchart of a method of transferring surgical robotic arms to a surgical table using a surgical robotic arm cart, according to an embodiment.

FIG. 6F is a flowchart of a method of a method 1600 of transporting and transferring surgical robotic arms to a surgical table using a surgical robotic arm cart, such as the arm carts 650 containing the rotary mechanism 670 as shown and described above with reference to FIGS. 6A-6E. The method 1600 includes loading one or more robotic arms onto an arm cart at 1602. For example the one or more robotic arms can be folded into a configuration suitable for transport and/or coupled to a rotary mechanism. The arm cart is then transported to an operating area and adjacent to a surgical table, at 1604.

The rotary mechanism can be turned at 1606, for example, as shown in FIGS. 6A and 6B. Turning the rotary mechanism, at 1606, can simultaneously move each of the robotic arms coupled to the rotary mechanism and can place one robotic arm in a deployment position (e.g., as shown in FIGS. 6B and 6C). Optionally, a selected robotic arm can be slid towards the surgical table, at 1608, for example, as shown in FIGS. 6D and 6E. In other embodiments, turning the rotary mechanism, can bring the selected robotic arm into position to be coupled to the surgical table. In such an embodiment, the act of turning the rotary mechanism can place the target joint J1 of a robotic arm in contact with a coupling mechanism of the surgical table and/or once a selected arm is in the deployment position the entire arm cart can be moved to place that robotic arm in contact with a coupling mechanism of the surgical table.

The robotic arm can be coupled to the surgical table, at 1612. The robotic arm can then be released from the arm cart, at 1614, and the arm cart is transported away from the operating area, at 1616. In some embodiments, if a second robotic arm has been loaded onto the arm cart, the arm cart can couple a first robotic arm to the surgical table, release the first robotic arm from the arm cart, and then be transported to a location adjacent another portion of the surgical table. The second robotic arm can then be coupled to the surgical table by repeating steps 1606-1614.

Figure 7:
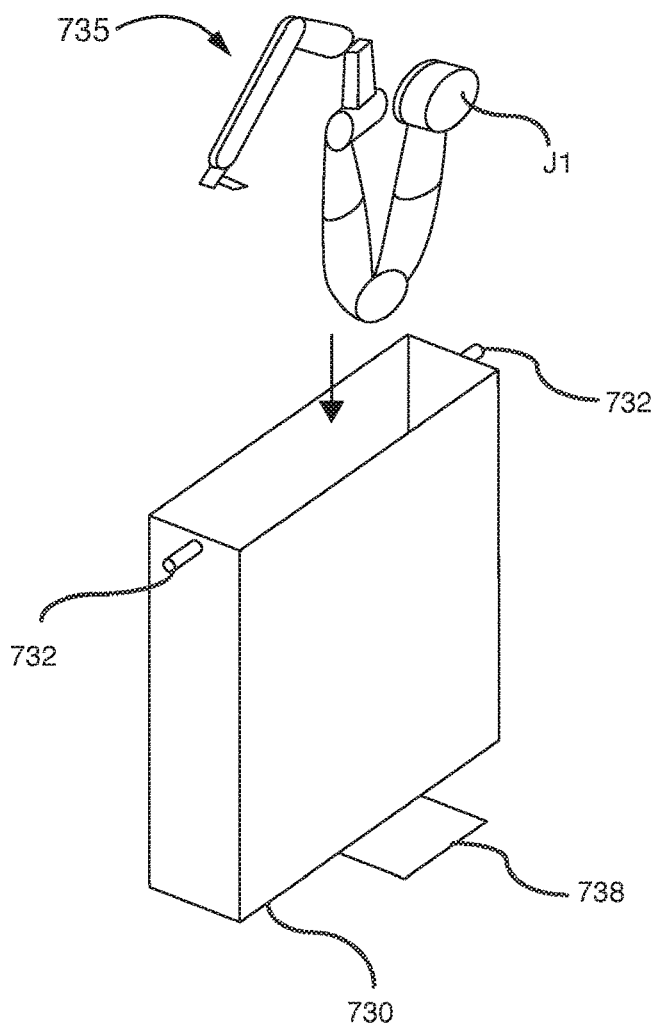
FIGS. 7 and 8 are schematic illustrations of arm cartridge configured to contain a robotic arm, according to two embodiments

FIG. 7A is a schematic illustration of a robotic arm 735 configured to be disposed and/or stored within a cartridge 730, according to an embodiment. The cartridge can, in turn, configured to be stored within an arm container of an arm cart, for example as shown and described above with reference to FIGS. 4A and 4B. As shown in FIG. 7, the robotic arm 735 can include multiple joints and can be articulated into a compact configuration for storage.

The robotic arm 735 includes a target joint J1, which can be disposed within a top portion of the arm cartridge 730 when the robotic arm 735 is in the stowed configuration. In this way, the robotic arm 735 can be extracted from and/or placed within the arm cartridge 730 by the target joint J1. For example, the robotic arm 735 can be placed into or removed from the arm cartridge 730 through an open (or openable) top (or other side) of the arm cartridge 730. The robotic arm 735 can be coupled to a surgical table via the target joint J1. For example, when transferring the robotic arm between the arm cartridge 730 and the surgical table, the arm cartridge 730 can be positioned adjacent the surgical table and the robotic arm 735 can be moved from the arm cartridge target joint J1—first or moved to the arm cartridge 735 target joint J1 last. In this way, the target joint J1 can be the first (and in some embodiments only) portion of the robotic arm 735 to contact the surgical table when the robotic arm 735 is transferred from the arm cartridge 730 to the surgical table and/or the last portion of the robotic arm 735 to be enter the arm cartridge 730 when the robotic arm 735 is transferred to the arm cartridge 730.

The arm cartridge 730 includes support features 732 operable to couple the arm cartridge 730 to an arm cart. The support features can include bearings, hinges, cylindrical joints, rotary joints, and/or any other suitable feature operable to allow the arm cartridge 730 to operable to allow the arm cartridge 730 to slide, pivot, rotate, or otherwise move within the arm cart.

Figure 8:
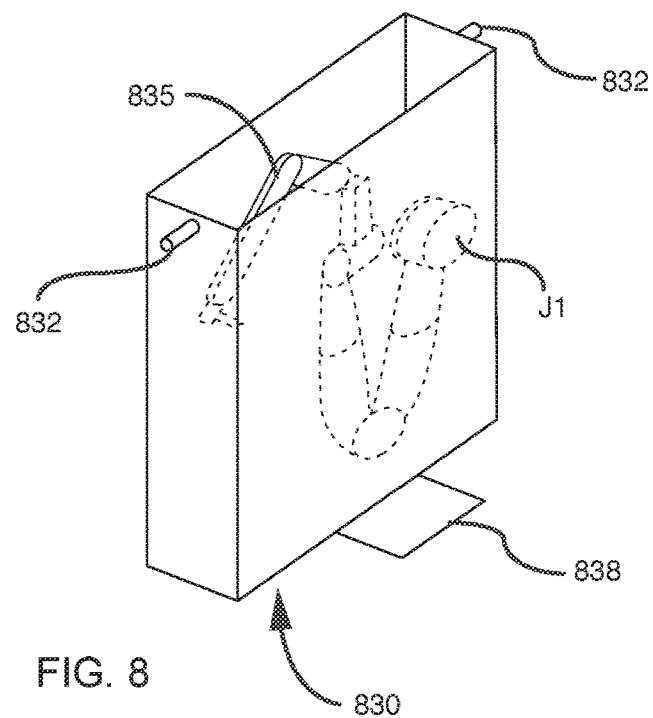

FIG. 8 is an illustration of an arm cartridge 830 containing a robotic arm 835, according to an embodiment. The arm cartridge 830 can be similar to the arm cartridge 730 described above. As illustrated in FIG. 8, the arm cartridge 830 contains journals 832 and a handle 838. In a storage configuration, the arm cartridge 830 can be operable to be disposed within an arm cart vertically (e.g., in an orientation in which the portion of the arm cartridge 830 containing the handle 838 is disposed below the portion of the arm cartridge 830 containing the journals 832). In use, the arm cartridge 830 can be grasped by the handle 838 and rotated about the journals 832, for example to deploy or receive the robotic arm 835.

While various embodiments have been described above, it should be understood that they have been presented by way of example only, and not limitation. For example, as shown and described with reference to FIG. 8, an arm cartridge 830 can include a handle. It should he understood that other arm cartridges and/or robotic arms described herein can include a handle or similar structure. It should further be understood that arm cartridges and/or robotic arms can be transported, loaded, unloaded, and otherwise manipulated by hand via a handle or similar structure. For example, arm cartridges and/or robotic arms can be manually removed from carried between locations, and/or loaded into arm carts by a handle or other similar structure.

Where methods described above indicate certain events occurring in certain order, the ordering of certain events may be modified. Additionally, certain of the events may be performed concurrently in a parallel process when possible, as well as performed sequentially as described above For example, in some embodiments, a robotic arm can be moved within the arm cart such that a coupling member associated with the robotic arm (e.g., a target joint J1) can be presented at a suitable location for engagement with a complementary coupling member associated with a table. For example, the arm cart can adjust the robotic arm to various height settings such that the robotic arm can cooperate with various surgical tables and/or various coupling portions of a surgical table at varying heights. For example, in some embodiments, the arm cart can perform a first macro phase of height adjustment within the arm cart in which the robotic arm cart is set to a high, medium, or low height range. The arm cart can then be moved into position relative to the surgical table such that the coupling member of the robotic arm is aligned with a coupling member associated with the surgical table with respect to the X axis and/or Y axis. Then, in a second micro phase of height adjustment, the arm cart can move the coupling member of the robotic arm cart up or down along the Z axis into engagement with the complementary coupling member of the surgical table. After the arm cart sets the robotic arm at the appropriate macro setting of high, medium, or low, the arm cart can be moved toward the surgical table. When the arm cart is properly aligned along the X axis and the Y axis, the coupling member can be lowered (along the Z axis) by the arm cart into engagement with a coupling member of the surgical table. Alternatively, when the arm cart is properly aligned along the X axis and the Y axis, the robotic arm can be raised into engagement with a coupling member of the surgical table.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

Some embodiments describe various features, axes, and/or directions as "horizontal" or "vertical." In general, the term "vertical" should be understood as a direction approximately (e.g., +/−15 degrees) parallel to the direction of gravity. Similarly, "horizontal" should be understood as a direction approximately (e.g., +/−15 degrees) normal to the direction of gravity and/or approximately parallel to a ground plane (e.g., a floor). Where components (e.g., robotic arms and/or arm cartridges) are described as vertical or horizontal, it should be understood as referring to a major axis of the component being oriented in the vertical or horizontal direction. When used to describe a robotic arm, a robotic arm is "horizontal" if joints of the robotic arm are primarily disposed in an approximately horizontal plane. A robotic arm is "vertical" if joints of the robotic arm are primarily disposed in an approximately vertical plane. When used to describe an arm cartridge, an arm cartridge is "vertical" if it contains (or is configured to contain) a robotic arm in a vertical orientation. An arm cartridge is "horizontal" if it contains (or is configured to contain) a robotic arm in a horizontal orientation.

What is claimed is:

1. An apparatus, comprising:
a plurality of robotic arms, each robotic arm from the plurality of robotic arms configured to be coupled to a surgical table; and
an arm cart configured to contain the plurality of robotic arms, a robotic arm from the plurality of robotic arms movable within the arm cart between a first storage position within the arm cart, a second storage position within the arm cart, and a deployment position, the robotic arm oriented vertically and disposed entirely within the arm cart in the first storage position and the second storage position, the robotic arm oriented horizontally and at least a portion of the robotic arm arranged to protrude from the arm cart in the deployment position such that the portion of the robotic arm is configured to mate with the surgical table.

2. The apparatus of claim 1, further comprising a release mechanism configured to release the robotic arm from the arm cart.

3. The apparatus of claim 1, wherein the robotic arm is configured to translate along a horizontal axis between the first storage position and the second storage position.

4. The apparatus of claim 1, wherein the robotic arm is configured to pivot about a horizontal axis between the second storage position and the deployment position.

5. The apparatus of claim 1, wherein:
the robotic arm is a first robotic arm, the apparatus further includes a second robotic arm from the plurality of robotic arms;
the second robotic arm is movable between a third storage position in a middle portion of the arm cart and a fourth storage position in a rear portion of the arm cart;
the second robotic arm configured to move from the third storage position to the fourth storage position before the first robotic arm is moved to the deployment position, the first robotic arm configured to pivot from the first storage position to the deployment position, the fourth storage position arranged to provide clearance for the first robotic arm to move into the deployment position.

6. The apparatus of claim 1, wherein:
the robotic arm is a first robotic arm, the apparatus further includes a second robotic arm from the plurality of robotic arms;
the deployment position is a first deployment position;
the second robotic arm is movable between a third storage position, a fourth storage position, and a second deployment position; and
the second robotic arm configured to move from the third storage position to the second deployment position when the first robotic arm is in the second storage position.

7. A method for transferring robotic arms to a surgical table, the method comprising:
moving an arm cart containing a plurality of robotic arms from a storage location to a surgical table;
pivoting a robotic arm from the plurality of robotic arms from a vertical storage position to a horizontal deployment position;
sliding the robotic arm horizontally towards the surgical table;
coupling the robotic arm to the surgical table; and
decoupling the robotic arm from the arm cart.

8. The method of claim 7, wherein the robotic arm is a first robotic arm from the plurality of robotic arms, and the robotic arm is coupled to a first position of the surgical table, the method further comprising:

moving the arm cart from the first location of the surgical table to a second location of the surgical table;

pivoting a second robotic arm from the plurality of robotic arms from a vertical storage position to a horizontal deployment position; and coupling the second robotic arm to the second position of the surgical table.

9. The method of claim 7, further comprising:

recoupling the robotic arm to the arm cart;

decoupling the robotic arm from the surgical table; and pivoting the robotic arm to the vertical storage position after decoupling the robotic arm from the surgical table.

10. The method of claim 7, wherein:

the robotic arm is a first robotic arm, and the first robotic arm is pivoted to the horizontal deployment position while a second robotic arm from the plurality of robotic arms is disposed within the arm cart, and the surgical table is a first surgical table, the method further comprising:

recoupling the first robotic arm to the arm cart decoupling the first robotic arm from the first surgical table;

pivoting the robotic arm to the vertical storage position after decoupling the first robotic arm from the first surgical table;

moving the arm cart to a second surgical table;

pivoting the second robotic arm a vertical storage position to a horizontal deployment position while the first robotic arm is disposed within the arm cart;

sliding the second robotic arm horizontally towards the second surgical table; and coupling the second robotic arm to the second surgical table.

\* \* \* \* \*